(12) United States Patent
Lo et al.

(10) Patent No.: US 9,051,616 B2
(45) Date of Patent: *Jun. 9, 2015

(54) DIAGNOSING FETAL CHROMOSOMAL ANEUPLOIDY USING MASSIVELY PARALLEL GENOMIC SEQUENCING

(71) Applicant: The Chinese University of Hong Kong, New Territories (HK)

(72) Inventors: Yuk-Ming Dennis Lo, Kowloon (HK); Rossa Wai Kwun Chiu, New Terrirtories (HK); Kwan Chee Chan, New Territories (HK)

(73) Assignee: The Chinese University of Hong Kong, New Territories (HK)

( * ) Notice: Subject to any disclaimer, the term of this patent is extended or adjusted under 35 U.S.C. 154(b) by 0 days.

This patent is subject to a terminal disclaimer.

(21) Appl. No.: 14/335,477

(22) Filed: Jul. 18, 2014

(65) Prior Publication Data

US 2014/0329696 A1    Nov. 6, 2014

Related U.S. Application Data

(63) Continuation of application No. 12/178,181, filed on Jul. 23, 2008.

(60) Provisional application No. 60/951,438, filed on Jul. 23, 2007.

(51) Int. Cl.
| | |
|---|---|
| *G01N 33/50* | (2006.01) |
| *C12Q 1/68* | (2006.01) |
| *G06F 19/18* | (2011.01) |
| *G06F 19/22* | (2011.01) |

(52) U.S. Cl.
CPC ............. C12Q 1/6883 (2013.01); G06F 19/18 (2013.01); *G06F 19/22* (2013.01); C12Q 1/6827 (2013.01); C12Q 1/6888 (2013.01); *C12Q 2600/154* (2013.01); *C12Q 2600/112* (2013.01); *C12Q 2600/156* (2013.01); *G01N 2800/387* (2013.01)

(58) Field of Classification Search
None
See application file for complete search history.

(56) References Cited

U.S. PATENT DOCUMENTS

| | | | |
|---|---|---|---|
| 5,641,628 A | 6/1997 | Bianchi | |
| 5,879,883 A | 3/1999 | Benson et al. | |
| 6,100,029 A | 8/2000 | Lapidus et al. | |
| 6,143,496 A | 11/2000 | Brown et al. | |
| 6,214,558 B1 | 4/2001 | Shuber et al. | |
| 6,258,540 B1 | 7/2001 | Lo et al. | |
| 6,391,559 B1 | 5/2002 | Brown et al. | |
| 6,440,706 B1 | 8/2002 | Vogelstein et al. | |
| 6,566,101 B1 | 5/2003 | Shuber et al. | |
| 6,632,655 B1 | 10/2003 | Mehta et al. | |
| 6,664,056 B2 | 12/2003 | Lo et al. | |
| 6,753,147 B2 | 6/2004 | Vogelstein et al. | |
| 6,927,028 B2 | 8/2005 | Dennis et al. | |
| 7,332,277 B2 | 2/2008 | Dhallan | |
| 7,442,506 B2 | 10/2008 | Dhallan | |
| 7,476,363 B2 | 1/2009 | Unger et al. | |
| 7,645,576 B2 | 1/2010 | Lo et al. | |
| 7,655,399 B2 | 2/2010 | Cantor et al. | |
| 7,704,687 B2 | 4/2010 | Wang et al. | |
| 7,727,720 B2 | 6/2010 | Dhallan et al. | |
| 7,838,647 B2 | 11/2010 | Hahn et al. | |
| 7,888,017 B2 | 2/2011 | Quake et al. | |
| 8,008,018 B2 | 8/2011 | Quake et al. | |
| 2001/0051341 A1 | 12/2001 | Lo et al. | |
| 2002/0164816 A1 | 11/2002 | Quake | |
| 2003/0022207 A1 | 1/2003 | Balasubramanian et al. | |
| 2003/0044388 A1 | 3/2003 | Dennis et al. | |
| 2003/0186255 A1 | 10/2003 | Williams et al. | |
| 2003/0204331 A1 | 10/2003 | Whitney et al. | |
| 2004/0096892 A1 | 5/2004 | Wang et al. | |
| 2004/0137470 A1 | 7/2004 | Dhallan | |
| 2004/0203037 A1 | 10/2004 | Lo et al. | |
| 2004/0209299 A1 | 10/2004 | Pinter et al. | |
| 2005/0003351 A1 | 1/2005 | Fejgin et al. | |
| 2005/0019792 A1 | 1/2005 | McBride et al. | |
| 2005/0037388 A1 | 2/2005 | Antonarakis et al. | |
| 2005/0129581 A1 | 6/2005 | McBride et al. | |

(Continued)

FOREIGN PATENT DOCUMENTS

| | | |
|---|---|---|
| EP | 0994963 B1 | 5/2003 |
| EP | 2161347 A2 | 3/2010 |

(Continued)

OTHER PUBLICATIONS

Stolovitzky, "Statistical analysis of MPSS measurements: Application to the study of LPS-activated macrophage gene expression," *PNAS*, Feb. 1, 2005, 102(5):1402-07, XP0055043869, ISSN: 0027-8424, DOI: 10.1 073/pnas.0406555102.

Meyers et al, "Analysis of the transcriptional complexity of *Arabidopsis thaliana* by massive parallel signature sequencing," *Nat. Biotech.*, Aug. 1, 2004, 22(8):1006-11, XP002438788, ISSN: 1087-0156, DOI: 10.1038/NBT992.

Extended European Search Report dated Nov. 23, 2012 in European Application No. 12175754.6, 6 pages.

(Continued)

*Primary Examiner* — Jason Sims
(74) *Attorney, Agent, or Firm* — Finnegan, Henderson, Farabow Garrett & Dunner LLP.

(57) ABSTRACT

Embodiments of this invention provide methods, systems, and apparatus for determining whether a fetal chromosomal aneuploidy exists from a biological sample obtained from a pregnant female. Nucleic acid molecules of the biological sample are sequenced, such that a fraction of the genome is sequenced. Respective amounts of a clinically-relevant chromosome and of background chromosomes are determined from results of the sequencing. A parameter derived from these amounts (e.g. a ratio) is compared to one or more cutoff values, thereby determining a classification of whether a fetal chromosomal aneuploidy exists.

6 Claims, 10 Drawing Sheets

(56) References Cited

U.S. PATENT DOCUMENTS

| | | |
|---|---|---|
| 2005/0145496 A1 | 7/2005 | Goodsaid et al. |
| 2005/0164241 A1 | 7/2005 | Hahn et al. |
| 2005/0221341 A1 | 10/2005 | Shimkets et al. |
| 2005/0221373 A1 | 10/2005 | Enzelberger et al. |
| 2005/0252773 A1 | 11/2005 | McBride et al. |
| 2006/0046258 A1 | 3/2006 | Lapidus et al. |
| 2006/0051775 A1 | 3/2006 | Bianchi et al. |
| 2006/0121452 A1 | 6/2006 | Dhallan |
| 2006/0252068 A1 | 11/2006 | Lo et al. |
| 2006/0252071 A1 | 11/2006 | Lo et al. |
| 2007/0059680 A1 | 3/2007 | Kapur et al. |
| 2007/0134658 A1 | 6/2007 | Bohmer |
| 2007/0202525 A1 | 8/2007 | Quake et al. |
| 2007/0207466 A1 | 9/2007 | Cantor et al. |
| 2007/0212689 A1 | 9/2007 | Bianchi et al. |
| 2007/0238105 A1 | 10/2007 | Barrett et al. |
| 2007/0275402 A1 | 11/2007 | Lo et al. |
| 2008/0020390 A1 | 1/2008 | Mitchell et al. |
| 2008/0026390 A1 | 1/2008 | Stoughton et al. |
| 2008/0038733 A1 | 2/2008 | Bischoff et al. |
| 2008/0050739 A1 | 2/2008 | Stoughton et al. |
| 2008/0070792 A1 | 3/2008 | Stoughton et al. |
| 2008/0071076 A1 | 3/2008 | Hahn et al. |
| 2008/0090239 A1 | 4/2008 | Shoemaker et al. |
| 2008/0096216 A1 | 4/2008 | Quake |
| 2008/0096766 A1 | 4/2008 | Lee |
| 2008/0113358 A1 | 5/2008 | Kapur |
| 2008/0124721 A1 | 5/2008 | Fuchs |
| 2008/0138809 A1 | 6/2008 | Kapur et al. |
| 2008/0153090 A1 | 6/2008 | Lo et al. |
| 2008/0182261 A1 | 7/2008 | Bianchi |
| 2008/0193927 A1 | 8/2008 | Mann et al. |
| 2008/0213775 A1 | 9/2008 | Brody et al. |
| 2008/0220422 A1 | 9/2008 | Shoemaker et al. |
| 2008/0299562 A1 | 12/2008 | Oeth et al. |
| 2009/0170114 A1 | 7/2009 | Quake et al. |
| 2009/0280492 A1 | 11/2009 | Stoughton et al. |
| 2009/0291443 A1 | 11/2009 | Stoughton et al. |
| 2010/0094562 A1 | 4/2010 | Shohat et al. |
| 2010/0112575 A1 | 5/2010 | Fan et al. |
| 2010/0216151 A1 | 8/2010 | Lapidus et al. |
| 2010/0216153 A1 | 8/2010 | Lapidus et al. |
| 2010/0291572 A1 | 11/2010 | Stoughton et al. |
| 2011/0003293 A1 | 1/2011 | Stoughton et al. |

FOREIGN PATENT DOCUMENTS

| | | |
|---|---|---|
| WO | WO03/020974 A2 | 3/2003 |
| WO | WO03/030823 | 4/2003 |
| WO | WO03/048295 A1 | 6/2003 |
| WO | WO2004/065629 A1 | 8/2004 |
| WO | WO2004/078999 A1 | 9/2004 |
| WO | WO2005/023091 A2 | 3/2005 |
| WO | WO2005/118852 A2 | 12/2005 |
| WO | WO2006/010610 A2 | 2/2006 |
| WO | WO2006/108101 A2 | 10/2006 |
| WO | WO2007/028155 A2 | 3/2007 |
| WO | WO2007/044091 A2 | 4/2007 |
| WO | WO2007/075836 A2 | 7/2007 |
| WO | WO2007/092473 A2 | 8/2007 |
| WO | WO2007/100911 A2 | 9/2007 |
| WO | WO2007/132166 A2 | 11/2007 |
| WO | WO2007/132167 A2 | 11/2007 |
| WO | WO2007/147073 A2 | 12/2007 |
| WO | WO2007/147074 A2 | 12/2007 |
| WO | WO2007/147076 A2 | 12/2007 |
| WO | WO2008/150368 | 12/2008 |
| WO | WO2009/013492 A1 | 1/2009 |
| WO | WO2009/013496 A1 | 1/2009 |
| WO | WO2009/019455 A2 | 2/2009 |
| WO | WO2009/037690 | 3/2009 |

OTHER PUBLICATIONS

Giurato et al., "An accurate pipeline for analysis of NGS data of small noncoding RNA" *EMBnet.Journal*, May 2012, 18(Suppl. A):100-01.

Green et al., "Analysis of one million base pairs of Neaderthal DNA," *Nature*, Nov. 16, 2006, 444:330-36.

Nannya, et al, "A robust algorithm for copy number detection using high-density oligonucleotide single nucleotide polymorphism genotyping arrays," *Cancer Res.* Jul. 15, 2005, 65:6071-79.

Noonan et al., "Sequencing and Analysis of Neadertal Genomic DNA," *Science*, Nov. 17, 2006, 314:1113-18.

Seo et al., "Four-color DNA sequencing by synthesis on a chip using photocleavable fluorescent nucleotides," *Proc. Nat. Acad. Sci.* Apr. 13, 2005, 102(17):5926-31.

Smith, et al., "Using quality scores and longer reads improves accuracy of Solexa read mapping," *BMC Bioinformatics*, Feb. 28, 2008, 9(128):1-8.

Thornley, "Analysis of Trace Data from Fluorescence Based Sanger Sequencing," (1997). Thesis, University of London Imperial College of Science, Technology and Medicine Department of Computing.

Sequenom, Inc. and Sequenom Center for Molecular Medicine LLC's Patent L. R. 4-2 Preliminary Claim Constructions and Extrinsic Evidence, *Verinata Health v. Sequenom*, No. 12-00865 (N.D. Cal. 2012), dated Oct. 26, 2012.

Sequenom, Inc. and Sequenom Center for Molecular Medicine LLC's Patent L. R. 3-3 Preliminary Invalidity Contentions for U.S. Patent Nos. 7,888,017, 8,006,018 and 8,195,415 and Patent L.R. 3-4 Document Production, *Verinata Health v. Sequenom*, No. 12-00865 (N.D. Cal. 2012), dated Sep. 28, 2012.

*Verinata Health, Inc. v. Sequenom, Inc.* Case 3:12-cv-00865-Si Document 58, pp. 1-6. Filed Nov. 21, 2012. Joint Claim Construction and Prehearing Statement Regarding Verinata Patents-in-Suit.

*Verinata Health, Inc. v. Sequenom, Inc.* Case 3:12-cv-00865-SI Document 58-1, pp. 1-47. Filed Nov. 21, 2012. Exhibit A for U.S. Patent 7,888,017 to Joint Claim Construction and Prehearing Statement.

*Verinata Health, Inc. v. Sequenom, Inc.* Case 3:12-cv-00865-SI Document 58-2, pp. 1-32. Filed Nov. 21, 2012. Exhibit B for U.S. Patent 8,008,018 to Joint Claim Construction and Prehearing Statement.

*Verinata Health, Inc. v. Sequenom, Inc.* Case 3:12-cv-00865-SI Document 58-3, pp. 1-14. Filed Nov. 21, 2012. Exhibit C for U.S. Patent 8,195,415 to Joint Claim Construction and Prehearing Statement.

*Verinata Health, Inc. v. Sequenom, Inc.* Case 3:12-cv-00865-SI Documents 60-2, pp. 5-90. Filed Nov. 21, 2012. Declaration of Dr. Michael L. Metzker Regarding Claim Construction.

*Verinata Health, Inc. v. Sequenom, Inc.* Case C-12-00865 SI, pp. 1-49. Served Nov. 21, 2012. Declaration of Stephen A. Brown, M.D. regarding claim construction of U.S. Patents 7,888,017 and 8,008,018.

Feinberg, Andrew, et al., "A Technique for Radiolabeling DNA Restriction Endonuclease Fragments to High Specific Activity," *Analytical Biochemistry*, Jul. 1, 1983, 132:6-13.

"Separation of RNA & DNA by Gel Filtration Chromatography," Edvotek, 1987, pp. 1-9.

Xiong, et al., "A simple, rapid, high-fidelity and cost-effective PCR-based two-step DNA synthesis method for long gene sequences," Nucleic Acids Research, Apr. 19, 2004, 32(12): e98-e107.

Zimmermann, et al., "Novel Real-Time Quantitative PCR Test for Trisomy 21 ," Jan. 1, 2002, *Clinical Chemistry*, American Association for Clinical Chemistry, 48(2): 362-63.

Pertl, et al., "Fetal DNA in Maternal Plasma: Emerging Clinical Applications," *Obstetrics and Gynecology*, Sep. 2001, 98(3): 483-90.

Zimmermann, "Molecular Diagnosis in Prenatal Medicine," Ph.D. Thesis, Jul. 6, 2004, pp. 1-19.

Vogelstein, et al., "Digital PCR," *PNAS*, Aug. 1999, 96: 9236-41.

Chan, et al. "Size Distributions of Maternal and Fetal DNA in Maternal Plasma," *Clinical Chemistry*, Jan. 2004, 50(1): 88-92.

Chiu, et al. "Non-invasive prenatal assessment of trisomy 21 by multiplexed maternal plasma DNA sequencing: large scale validity study." *BMJ*, Dec. 14, 2010, c7401-c7410.

Chiu et al., Noninvasive prenatal diagnosis of fetal chromosomal aneuploidy by massively parallel genomic sequencing of DNA in maternal plasma. *PNAS*, Dec. 23, 2008; 105(51): 20458-63.

(56) References Cited

OTHER PUBLICATIONS

Dressman, et al., "Transforming single DNA molecules into fluorescent magnetic particles for detection and enumeration of genetic variations," *PNAS*, Jul. 2003, 100(15): 8817-22.
Dhallan et al., "A non-invasive test for prenatal diagnosis based on fetal DNA present in maternal blood" a preliminary study. *The Lancet*. Feb. 2, 2007, 369:474-81.
Ottesen et al., "Microfluidic Digital PCR Enables Multigene Analysis of Individual Environmental Bacteria," *Science*, Dec. 2006, 314: 1464-67.
Enders et al., "The Concentration of Circulating Corticotropin-releasing Hormone mRNA in Maternal Plasma is Increased in Preeclampsia," *Clinical Chemistry*, May 2003, 49(5):727-731.
EPO Examination Report, EP Application No. 07 763 674.4, Dec. 21, 2010, 3 pages.
EPO Search Report, EP Application No. 07 763 674.4, Jul. 31, 2009, 10 pages.
Chan, et al., "DNA Mapping Using Microfluidic Stretching and Single-Molecule Detection of Fluorescent Site-Specific Tags," *Genome Research*, Jun. 2004, 14:1137-46.
European Search Report dated Dec. 21, 2009 for Application No. 07798579.4, 3 pages.
European search report dated Dec. 22, 2009 for Application No. 07798580.2, 3 pages.
European search report dated Dec. 22, 2009 for Application No. 07784444.7, 4 pages.
European search report dated Nov. 9, 2009 for Application No. 07784442.1, 3 pages.
Lun, et al., "Microfluidics Digital PCR Reveals a Higher Than Expected Fraction of Fetal DNA in Maternal Plasma," *Clin. Chem.*, Oct. 2008, 54(10): 1664-72.
Diehl, et al., "Digital Quantification of Mutant DNA in Cancer Patients," *Curr. Opin. Oncol.*, Jan. 2007, 19:36-42.
Fan, et al., "Detection of Aneuploidy with Digital Polymerase Chain Reaction," *Analytical Chemistry*, Oct. 1, 2007, 79(19): 7576-79.
Fan, et al., "Microfluidic Digital PCR Enables Rapid Prenatal Diagnosis of Fetal Aneuploidy," *American Journal of Obstetrics & Gynecology*, May 2009, pp. 543e1-543e7.
Fan, et al., "Noninvasive Diagnosis of Fetal Aneuploidy by Shotgun Sequencing DNA from Maternal Blood," *PNAS*, Oct. 21, 2008, 105:16266-71.
Rahil, et al., "Rapid Detection of Common Autosomal Aneuploidies by Quantitative Fluorescent PCR on Uncultured Amniocytes," *Eur. J. Hum. Genetics*, 2002, 10:462-66.
Hong, et al., "A Nanoliter-scale Nucleic Acid Processor with Parallel Architecture," *Nat. Biotech.*, 2004, 22(4):435-39.
Braslavsky, at al., "Sequence information can be obtained from single DNA molecules," *PNAS*, Apr. 2003, 100(7):3960-64.
Hromadnikova, et al., "Quantitative Analysis of DNA Levels in Maternal Plasma in Normal and Down Syndrome Pregnancies," *Bio Med Central*, May 2002, 1-5.
International Preliminary Report on Patentability Dated Oct. 14, 2008 for PCT/US2007/003209, 7 pages.
International Search Report and Written Opinion for PCT/US2007/003209, Sep, 18, 2008, 2 pages.
International Search Report and Written Opinion for PCT/US2009/057136, Mar. 16, 2010, 3 pages.
Shendure, et al., "Next-generation DNA Sequencing," *Nature Biotech.*, Oct. 2008, 26(10):1135-45.
Hong, et al., "Molecular biology on a microfluidic chip," *Journal of Physics: Condensed Matter*, Apr. 19, 2006, 18:S691-S701.
Marcus, et al., "Microfluidic Single-Cell mRNA Isolation and Analysis," *Journal of the American Chemical Society*, Mar. 2006, pp. A-F.
Marcus, et al., "Parallel Picoliter RT-PCR Assays Using Microfluidics." *Analytical Chemistry*, Feb. 1, 2006, 78(3): 956-58.
Uitto, at al., "Probing the Fetal Genome: Progress in Non-Invasive Prenatal Diagnosis," *Trends in Molecular Medicine*, Aug. 2003, 9(8): 339-43.
Zhu, et al., "Single Molecule Profiling of Alternative Pre-mRNA Splicing," *Science*, Aug. 2003, 301: 836-38.
Kasakov, et al. "Extracellular DNA in the blood of pregnant women," *Tsitologiia*, 1995; 37(3):232-6. (English translation only).
Poon, et al., "Circulating Fetal DNA in Maternal Plasma," *Clin. Chim. Acta*, 2001, 313:151-55.
Leutwyler, "Mapping Chromosomes 21," *Scientific American*, May 15, 2000, 2 pages.
Maloney, et al., "Microchimerism of Maternal Origin Persists into Adult Life," *J. Clin. Investigation*, Jul. 1999, 104:41-47.
Martin, et al., "A Method for Using Serum or Plasma as a Source of DNA for HLA Typing," *Human Immunol.*, Feb. 1992, 33:108-13.
Nelson, et al., "Genotyping fetal DNA by non-invasive means: extraction from maternal plasma," *Vox Sanguinis*, Feb. 2001, 80:112-16.
Office Action (*ex parte Quayle*) dated May 13, 2011 for U.S. Appl. No. 11/763,421 with pending claims, 8 pages.
Office Action dated Dec. 1, 2009 for U.S. Appl. No. 11/763,426 with pending claims, 13 pages.
Office Acton dated Dec. 3, 2008 for U.S. Appl. No. 11/763,426 with pending claims, 22 pages.
Office Action dated Dec. 31, 2009 for U.S. Appl. No. 11/763,421 with pending claims, 16 pages.
Office Action dated Feb. 15, 2011 for U.S. Appl. No. 11/763,426 with pending claims, 13 pages.
Office Action dated Jan. 12, 2009 for U.S. Appl. No. 11/763,133 with pending claims, 12 pages.
Office Action dated Jul. 10, 2009 for U.S. Appl. No. 11/763,421 with pending claims, 26 pages.
Office Action dated Jun. 14, 2010 for U.S. Appl. No. 11/763,426 with pending claims, 16 pages.
Office Action dated Mar. 11, 2010 for U.S. Appl. No. 11/765,245 with pending claims, 19 pages.
Office Action dated Mar. 29, 2011 for U.S. Appl. No. 11/763,245 with pending claims, 25 pages.
Office Action dated Mar. 4, 2009 for U.S. Appl. No. 11/228,454 with pending claims, 16 pages.
Office Action dated May 18, 2011 for U.S. Appl. No. 12/413,467 with pending claims, 39 pages.
Office Action dated May 6, 2011 for U.S. Appl. No. 11/763,133 with pending claims, 46 pages.
Office Action dated Nov. 3, 2009 for U.S. Appl. No. 11/763,133 with pending claims, 17 pages.
Office Action dated Sep. 23, 2009 for EP Application No. EP07763674.4 with pending claims, 5 pages.
Office Action dated Jun. 7, 2012 for U.S. Appl. No. 12/178,181, 9 pages.
Sykes, et al., "Quantitation of Targets for PCR by Use of Limiting Dilution," *BioTechniques*, Sep. 1992, 13(3):444-49.
Pohl, et al., "Principle and Applications of Digital PCR," *Expert Reviews in Molecular Diagnosis*, Jan. 2004, 4:41-47.
Sparkes, et al., "New Molecular Techniques for the Prenatal Detection of Chromosomal Aneuploidy," *JOGC*, Jul. 2008, 210: 617-21.
White III, et al., "Digital PCR Provides Sensitive and Absolute Calibration for High Throughput Sequencing," *BMC Genomics*, Mar. 19, 2009, 10:116-45.
Chiu, et al., "Effects of Blood-Processing Protocols on Fetal and Total DNA Quantification in Maternal Plasma," *Clinical Chemistry*, Sep. 2001, 47(9):1607-13.
Kimura, et al., "The DYRK1A gene, encoded in chromosome 21 Down syndrome critical region, bridges between beta.-amyloid production and tau phosphorylation in Alzheimer disease," *Human Molecular Genetics*, Nov. 29, 2006, 16(1):15-23.
Tufan, et al., "Analysis of Cell-Free Fetal DNA from Maternal Plasma and Serum Using a Conventional Multiplex PCR: Factors Influencing Success," Turk J Med Sci, Nov. 19, 2004, 35:85-92.
Sehnert, et al., "Optimal Detection of Fetal Chromosomal Abnormalities by Massively Parallel DNA Sequencing of Cell-Free Fetal DNA from Maternal Blood." *Clin Chem*. Apr. 25, 2011, 8 pages [Epub ahead of print].
Hahn, et al., "Prenatal Diagnosis Using Fetal Cells and Cell-Free Fetal DNA in Maternal Blood: What is Currently Feasible?" *Clinical Obstetrics and Gynecology*, Sep. 2002, 45(3):649-56.
Solexa Genome Analysis System Product Brochure. 2006; 2 pages.

(56) References Cited

OTHER PUBLICATIONS

Emanuel, et al., "Amplification of Specific Gene Products from Human Serum," *GATA*, Nov. 1993, 10(6):144-46.
Tanaka, et al., "Genome-wide expression profiling of mid-gestation placenta and embryo using a 15,000 mouse developmental cDNA microarray," *PNAS*, Aug. 2000, 97(16):9127-32.
Tettelin, at al., "The nucleotide sequence of *Saccharomyces cerevisiae* chromosome VII," *Nature* May 29, 1997, 387:81-84.
Cirigliano, et al., "Clinical Application of Multiplex Quantitative Fluorescent Polymerase Chain Reaction (QF-PCR) for the Rapid Prenatal Detection of Common Chromosome Aneuploides," *Mol. Hum. Reproduction*, Oct. 2001, 7(10):1001-06.
Voelkerding, et al., "Digital fetal aneuploidy diagnosis by next-generation sequencing," *Clin. Chem.* Mar. 2010; 56(3):336-38.
Li, et al., "Size Separation of Circulatory DNA in Maternal Plasma Permits Ready Detection of Fetal DNA Polymorphisms," Jun. 2004, *Clin. Chem.*, 50(6):1002-11.
Lo, et al., "Plasma placental RNA allelic ratio permits noninvasive prenatal chromosomal aneuploidy detection," *Nature Medicine*, Jan. 2007, 13(2):218-23.
Lo, et al., "Prenatal diagnosis: progress through plasma nucleic acids," *Nature*, Jan. 2007, 8:71-76.
Lo, et al., "Presence of fetal DNA in maternal plasma and serum," *The Lancet*, Aug. 16, 1997, 350: 485-87.
Lo, et al., "Digital PCR for the molecular detection of fetal chromosomal aneuploidy," *PNAS*, Aug. 7, 2007, 104(32):13116-21.
Lo, et al., "Quantitative Analysis of Fetal NA in Maternal Plasma and Serum: Implications for Noninvasive Prenatal Diagnosis," *Am J. Hum. Genet.*, Apr. 1998, 62:768-75.
Lo, at al., "Detection of fetal RhO sequence from peripheral blood of sensitized RhDGU negative pregnant women," *British Journal of Haematology*, Jul. 1994, 87: 658-60.
Lo, et al., "Detection of single-copy fetal DNA sequence from maternal blood," *The Lancet*, Jun. 16, 1990, 365:1463-64.
Lo, et al., "Fetal DNA in Maternal Plasma," *Ann. N.Y. Acad. Sci*, Apr. 2000, 906:141-47.
Lo, et al., "Prenatal Sex Determination by DNA Amplification from Maternal Peripheral Blood," *The Lancet*, Dec. 9, 1989, pp. 1363-1365.
Lo, "Noninvasive prenatal detection of fetal chromosomal aneuploidies by maternal plasma nucleic acid analysis: a review of the current state of the art," *BJOG*, Jan. 2009, 116:152-57.
Yang et al., "Prenatal Diagnosis of Trisomy 21 by Real-time Quantitative Polymerase Chain Reaction with Amplification of Small Tandem Repeats and S100B in Chromosome 21," *Yonsei Medical Journal*, Apr. 30, 2005, 46(2):193-97.
Zavala, et al., "Genomic GC content prediction in prokaryotes from a sample of genes," *Gene* Sep. 12, 2005, 357(2):137-43.
Dhallan, et al., "A non-invasive test for prenatal diagnosis based on fetal DNA present in maternal blood: a preliminary study." Feb. 10, 2007, *The Lancet*, 369: 474-81.
Fan, et al., "Detection of Aneuploidy with Digital PCR"; Department of AB Bioengineering, Stanford University and Howard Hughes Medical Institute, submitted on May 8, 2007, 14 pages.
European Examination Report Dated Jul. 13, 2010 issued in related European Application No. 08776043.5, filed Jul. 23, 2008.
Beck, et al.; "Profile of the Circulating DNA in Apparently Healthy individuals"; Apr. 2009, *Clinical Chemistry*, 55(4):730-38.
Fan, et al.; "Noninvasive diagnosis of fetal aneuploidy by shotgun sequencing DNA from maternal blood"; *PNAS*, Oct. 21, 2008, 105(42): 16286-71.
Bischoff, et al.; "Cell-Free Fetal DNA and Intact Fetal Cells in Maternal Blood Circulation: Implications for First and Second Trimester Non-Invasive Prenatal Diagnosis;" Nov. 1, 2002; *Human Reproduction Update*; 8(6): 493-500.
Lo, et al., "Prenatal Diagnosis: Progress Through Plasma Nucleic Acids;" Jan. 1, 2007; *Nature Reviews Genetics*; 8: 71-77.
Lo, et al.; "Digital PCR for the Molecular Detection of Fetal Chromosomal Aneuploidy;" Aug. 7, 2007; *PNAS*: 104(32): 13116-21.

Lo, et al., "Noninvasive Prenatal Diagnosis of Fetal Chromosomal Aneuploidies by Maternal Plasma Nucleic Acid Analysis:" *Clinical Chemistry*; Jan. 17, 2008; 54(3): 461-66.
Lo, et al., "Plasma Placental RNA Allelic Ratio Permits Noninvasive Prenatal Chromosomal Aneuploidy Detection," Feb. 2007; *Nature Medicine*; 13(2):218-23.
Shih, et al.; "Evidence that Genetic Instability Occurs at an Early Stage of Colorectal Tumorigenesis;" Feb. 1, 2002; *Cancer Research*; 61:816-22.
Tong, et al.; "Noninvasive Prenatal Detection of Fetal Trisomy 18 by Epigenetic Allelic Ratio Analysis in Maternal Plasma: Theoretical and Empirical Considerations;" Oct. 13, 2006; *Clinical Chemistry*; 52(12):2194-2202.
Zhong, et al.; "Fetal DNA in Maternal Plasma is Elevated in Pregnancies with Aneuploid Fetuses;" Oct. 1, 2000; *Prenatal Diagnosis*; 20(10):795-98.
Zhou, et al.; "Counting Alleles to Predict Recurrence of Early-Stage Colorectal Cancers:" Jan. 19, 2002; *The Lancet*; 359(9302):219-25.
Bentley, "Whole-genome re-sequencing"; Dec. 2006, *Current Opinion in Genetics & Development*, vol. 16:545-52.
Brenner et al., "Gene Expression Analysis by Massively Parallel Signature Sequencing (MPSS) on Microbead Arrays," Jun. 2000, *Nat. Biotech.*, 18:630-34.
Campbell et al., "Identification of Somatically Acquired Rearrangements in Cancer Using Genome-Wide Massively Parallel Paired-End Sequencing," Jun. 2008, *Nature Genetics*, 40(6):722-29.
Chan et al., "Hypermethylated *RASSFIA* in Maternal Plasma: A Universal Fetal DNA Marker that Improves the Reliability of Noninvasive Prenatal Diagnosis," Dec. 2006, *Clin. Chem.*, 52:2211-18.
Dear, "One by one: Single molecule tools for genomics"; Jan. 2003, *Briefings in Functional Genomics and Proteomics*, 1(4):397-416.
Harris et al., "Single-Molecule DNA Sequencing of a Viral Genome," Apr. 4, 2008, *Science*, 320:106-09.
Korshunova et al., "Massively Parallel Bisulphate Pyrosequencing Reveals the Molecular Complexity of Breast Cancer-Associated Cytosine-Methylation Patterns Obtained from Tissue and Serum DNA," Nov. 21, 2007, *Genome Research*, 18:19-29.
Margulies, et al.; "Genome sequencing in microfabricated high-density picolitre reactors"; Sep. 15, 2005, *Nature*, 437:376-80.
Meyer et al., "From Micrograms to Picograms: Quantitative PCR Reduces the Material Demands of High-Throughput Sequencing," Dec. 15, 2007, *Nucleic Acids Research*, 36(1):1-6.
Reinartz et al., "Massively Parallel Signature Sequencing (MPSS) as a Tool for In-Depth Quantitative Gene Expression Profiling in All Organisms," Feb. 2002, *Briefings in Functional Genomics and Proteomics*, 1(1):95-104.
Soni, et al.; "Progress toward Ultrafast DNA Sequencing Using Solid-State Nanopores"; Nov. 2007, *Clinical Chemistry*, 53:1996-2001.
Wheeler, et al., "The complete genome of an individual by massively parallel DNA sequencing"; Apr. 17, 2008, *Nature*, 452:872-77.
Larabee, et al., "Microarray analysis of cell-free fetal DNA in amniotic fluid: a prenatal molecular karyotype," *American Journal of Human Genetics*, American Society of Human Genetics, Chicago, IL, Sep. 1, 2004, 75(3):485-91.
Li, et al., "Size separation of circulatory DNA in maternal plasma permits ready detection of fetal DNA polymorphisms," *Clin. Chem.*, American Assoc. for Clin. Chem., Washington, DC, Jun. 1, 2004, 50(6):1002-1011.
Ding, et al., "MS Analysis of Single-Nucleotide Differences in Circulating Nucleic Acids: Application to Noninvasive Prenatal Diagnosis," *PNAS*, Jul. 20, 2004, 101(29): 10762-67.
Reed, et al., "Non-Invasive Determination of the Paternal HLA Haplotype of a Fetus Using Kinetic PCR to Detect Fetal Microchimerism in Maternal Plasma," *Bone Marrow Transplantation*, Mar. 2, 2002, 29(6): 527-29.
Chiu, et al., "Non-Invasive Prenatal Diagnosis by Single Molecule Counting Technologies," *Trends in Genetics*, Jul. 1, 2009, 25(7): 324-31.
Lun, et al., "Noninvasive Prenatal Diagnosis of Monogenic Diseases by Digital Size Selection and Relative Mutation Dosage on DNA in Maternal Plasma," *PNAS*, Dec. 16, 2008, 105(50): 19920-19925.

(56) References Cited

OTHER PUBLICATIONS

Peter, et al., "Cell-Free DNA Fragmentation Patterns in Amniotic Fluid Identify Genetic Abnormalities and Changes Due to Storage," *Diagn. Mol. Pathol.*, Sep. 2008, 17(3): 185-90.

Lapaire, et al., "Larger Columns and Change of Lysis Buffer Increase the Yield of Cell-Free DNA Extracted from Amniotic Fluid," Letters to the Editor, *Clin. Chem.*, Jan. 2006, 52(1): 156-57.

Lapaire, et al., "Cell-Free Fetal DNA in Amniotic Fluid: Unique Fragmentation Signatures in Euploid and Aneuploid Fetusus," *Clin. Chem.*, Mar. 2007, 53(3): 405-11.

Lapaire, et al., "Array-CGH Analysis of Cell-Free Fetal DNA in 10 mL of Amniotic Fluid Supernatant," *Prenatal Diagnosis*, May 17, 2007, 27: 616-21.

Bianchi, et al., "Large Amounts of Cell-Free DNA are Present in Amniotic Fluid," *Clin. Chem.*, Oct. 2001, 47(10): 1867-69.

Lecoeur, "Nuclear Apoptosis Detection by Flow Cytometry: Influence of Endogenous Endonucleases," *Experimental Cell Research*, Jul. 1, 2002, 277: 1-14.

Mann et al., "Strategies for the Rapid Prenatal Diagnosis of Chromosome Aneuploidy," *European Journal of Human Genetics*, Dec. 2004, 12: 907-15.

| Sample | Total No. of Sequenced Tags | Total No. of Sequenced Basepairs | Proportion of the Human Genome (%) | U0 Count | U0 Count / Total Count (%) | No. of U0 Sequenced Basepairs | U0 Proportion of the Human Genome (%) |
|---|---|---|---|---|---|---|---|
| Sample 1 T21 | 1.12E+07 | 4.02E+08 | 13.4 | 1.93E+06 | 17.3 | 6.94E+07 | 2.31 |
| Sample 2 T21 | 1.04E+07 | 3.73E+08 | 12.4 | 1.80E+06 | 17.4 | 6.50E+07 | 2.17 |
| Sample 3 T21 | 8.90E+06 | 3.20E+08 | 10.7 | 2.09E+06 | 23.4 | 7.51E+07 | 2.50 |
| Sample 4 T21 | 1.02E+07 | 3.69E+08 | 12.3 | 2.23E+06 | 21.7 | 8.02E+07 | 2.67 |
| Sample 5 euploid | 1.06E+07 | 3.83E+08 | 12.8 | 2.12E+06 | 19.9 | 7.62E+07 | 2.54 |
| Sample 6 euploid | 9.58E+06 | 3.45E+08 | 11.5 | 1.91E+06 | 20.0 | 6.88E+07 | 2.29 |
| Sample 7 euploid | 9.55E+06 | 3.44E+08 | 11.5 | 2.01E+06 | 21.0 | 7.22E+07 | 2.41 |
| Sample 8 euploid | 9.09E+06 | 3.27E+08 | 10.9 | 2.09E+06 | 23.0 | 7.53E+07 | 2.51 |

| Sequenced tag order | Sample 1 T21 | Sample 2 T21 | Sample 3 T21 | Sample 4 T21 | Sample 5 Euploid | Sample 6 Euploid | Sample 7 Euploid | Sample 8 Euploid |
|---|---|---|---|---|---|---|---|---|
| 1 | 9796394 | 9798087 | 9798123 | 9795700 | 9797841 | 9795972 | 9796536 | 9795601 |
| 2 | 9797424 | 9798402 | 9798250 | 9797860 | 9798176 | 9796549 | 9796863 | 9797404 |
| 3 | 9797438 | 9798708 | 9798715 | 9797864 | 9798835 | 9797359 | 9798161 | 9798117 |
| 4 | 9798112 | 9799733 | 9799467 | 9798106 | 9800315 | 9797418 | 9798401 | 9798175 |
| 5 | 9798394 | 9799852 | 9799730 | 9799209 | 9800385 | 9797446 | 9798722 | 9798387 |
| 6 | 9798729 | 9800362 | 9799788 | 9799440 | 9800554 | 9797860 | 9799752 | 9798816 |
| 7 | 9798768 | 9800914 | 9799834 | 9799440 | 9800820 | 9798062 | 9800317 | 9799732 |
| 8 | 9798816 | 9801528 | 9800332 | 9799741 | 9800829 | 9798135 | 9800800 | 9800144 |
| 9 | 9799421 | 9801779 | 9800869 | 9799812 | 9800832 | 9798707 | 9801380 | 9800421 |
| 10 | 9799464 | 9803801 | 9800881 | 9799833 | 9800866 | 9798715 | 9801699 | 9800827 |

FIG. 8A

| Sequenced tag order | Sample 1 T21 | Sample 2 T21 | Sample 3 T21 | Sample 4 T21 | Sample 5 Euploid | Sample 6 Euploid | Sample 7 Euploid | Sample 8 Euploid |
|---|---|---|---|---|---|---|---|---|
| 1 | 14469232 | 14510976 | 14510792 | 14510867 | 1443468 | 14510711 | 14512069 | 14510996 |
| 2 | 14503781 | 14511307 | 14510807 | 14511312 | 14506660 | 14510835 | 14512407 | 14522947 |
| 3 | 14510805 | 14511512 | 14511816 | 14511983 | 14511219 | 14511308 | 14522879 | 14530478 |
| 4 | 14510824 | 14511755 | 14511816 | 14522914 | 14511328 | 14511354 | 14609732 | 14565255 |
| 5 | 14510965 | 14511774 | 14512410 | 14522978 | 14511377 | 14511703 | 14628248 | 14609733 |
| 6 | 14511369 | 14512067 | 14522944 | 14523028 | 14511432 | 14511703 | 14675246 | 14628261 |
| 7 | 14511702 | 14512190 | 14523047 | 14565245 | 14511597 | 14512184 | 14675250 | 14668784 |
| 8 | 14511738 | 14522891 | 14564769 | 14628257 | 14511755 | 14512204 | 14680184 | 14680163 |
| 9 | 14523000 | 14539630 | 14565205 | 14635374 | 14512204 | 14524806 | 14692539 | 14689547 |
| 10 | 14524823 | 14541260 | 14565251 | 14665101 | 14512204 | 14565230 | 14694114 | 14689592 |

FIG. 8B

DIAGNOSING FETAL CHROMOSOMAL ANEUPLOIDY USING MASSIVELY PARALLEL GENOMIC SEQUENCING

CLAIM OF PRIORITY

This application is a continuation of application Ser. No. 12/178,181, filed Jul. 23, 2008, pending, which claims priority to U.S. Provisional Application No. 60/951,438, filed Jul. 23, 2007, both of which are incorporated by reference in their entirety.

CROSS-REFERENCES TO RELATED APPLICATIONS

The present application is also related to concurrently filed non-provisional application entitled "DETERMINING A NUCLEIC ACID SEQUENCE IMBALANCE," U.S. application Ser. No. 12/178,116, the entire contents of which are herein incorporated by reference for all purposes.

FIELD OF THE INVENTION

This invention generally relates to the diagnostic testing of fetal chromosomal aneuploidy by determining imbalances between different nucleic acid sequences, and more particularly to the identification of trisomy 21 (Down syndrome) and other chromosomal aneuploidies via testing a maternal sample (e.g. blood).

BACKGROUND

Fetal chromosomal aneuploidy results from the presence of abnormal dose(s) of a chromosome or chromosomal region. The abnormal dose(s) can be abnormally high, e.g. the presence of an extra chromosome 21 or chromosomal region in trisomy 21; or abnormally low, e.g. the absence of a copy of chromosome X in Turner syndrome.

Conventional prenatal diagnostic methods of a fetal chromosomal aneuploidy, e.g., trisomy 21, involve the sampling of fetal materials by invasive procedures such as amniocentesis or chorionic villus sampling, which pose a finite risk of fetal loss. Noninvasive procedures, such as screening by ultrasonography and biochemical markers, have been used to risk-stratify pregnant women prior to definitive invasive diagnostic procedures. However, these screening methods typically measure epiphenomena that are associated with the chromosomal aneuploidy, e.g., trisomy 21, instead of the core chromosomal abnormality, and thus have suboptimal diagnostic accuracy and other disadvantages, such as being highly influenced by gestational age.

The discovery of circulating cell-free fetal DNA in maternal plasma in 1997 offered new possibilities for noninvasive prenatal diagnosis (Lo, Y M D and Chiu, R W K 2007 Nat Rev Genet 8, 71-77). While this method has been readily applied to the prenatal diagnosis of sex-linked (Costa, J M et al. 2002 N Engl J Med 346, 1502) and certain single gene disorders (Lo, Y M D et al. 1998 N Engl J Med 339, 1734-1738), its application to the prenatal detection of fetal chromosomal aneuploidies has represented a considerable challenge (Lo, Y M D and Chiu, R W K 2007, supra). First, fetal nucleic acids co-exist in maternal plasma with a high background of nucleic acids of maternal origin that can often interfere with the analysis of fetal nucleic acids (Lo, Y M D et al. 1998 Am J Hum Genet 62, 768-775). Second, fetal nucleic acids circulate in maternal plasma predominantly in a cell-free form, making it difficult to derive dosage information of genes or chromosomes within the fetal genome.

Significant developments overcoming these challenges have recently been made (Benachi, A & Costa, J M 2007 Lancet 369, 440-442). One approach detects fetal-specific nucleic acids in the maternal plasma, thus overcoming the problem of maternal background interference (Lo, Y M D and Chiu, R W K 2007, supra). Dosage of chromosome 21 was inferred from the ratios of polymorphic alleles in the placenta-derived DNA/RNA molecules. However, this method is less accurate when samples contain lower amount of the targeted nucleic acid and can only be applied to fetuses who are heterozygous for the targeted polymorphisms, which is only a subset of the population if one polymorphism is used.

Dhallan et al (Dhallan, R, et al. 2007, supra Dhallan, R, et al. 2007 Lancet 369, 474-481) described an alternative strategy of enriching the proportion of circulating fetal DNA by adding formaldehyde to maternal plasma. The proportion of chromosome 21 sequences contributed by the fetus in maternal plasma was determined by assessing the ratio of paternally-inherited fetal-specific alleles to non-fetal-specific alleles for single nucleotide polymorphisms (SNPs) on chromosome 21. SNP ratios were similarly computed for a reference chromosome. An imbalance of fetal chromosome 21 was then inferred by detecting a statistically significant difference between the SNP ratios for chromosome 21 and those of the reference chromosome, where significant is defined using a fixed p-value of ≤0.05. To ensure high population coverage, more than 500 SNPs were targeted per chromosome. However, there have been controversies regarding the effectiveness of formaldehyde to enrich fetal DNA to a high proportion (Chung, G T Y, et al. 2005 Clin Chem 51, 655-658), and thus the reproducibility of the method needs to be further evaluated. Also, as each fetus and mother would be informative for a different number of SNPs for each chromosome, the power of the statistical test for SNP ratio comparison would be variable from case to case (Lo, Y M D & Chiu, R W K, 2007 Lancet 369, 1997). Furthermore, since these approaches depend on the detection of genetic polymorphisms, they are limited to fetuses heterozygous for these polymorphisms.

Using polymerase chain reaction (PCR) and DNA quantification of a chromosome 21 locus and a reference locus in amniocyte cultures obtained from trisomy 21 and euploid fetuses, Zimmermann et al (2002 Clin Chem 48, 362-363) were able to distinguish the two groups of fetuses based on the 1.5-fold increase in chromosome 21 DNA sequences in the former. Since a 2-fold difference in DNA template concentration constitutes a difference of only one threshold cycle (Ct), the discrimination of a 1.5-fold difference has been the limit of conventional real-time PCR. To achieve finer degrees of quantitative discrimination, alternative strategies are needed.

Digital PCR has been developed for the detection of allelic ratio skewing in nucleic acid samples (Chang, H W et al. 2002 J Natl Cancer Inst 94, 1697-1703). Digital PCR is an amplification based nucleic acid analysis technique which requires the distribution of a specimen containing nucleic acids into a multitude of discrete samples where each sample containing on average not more than about one target sequence per sample. Specific nucleic acid targets are amplified with sequence-specific primers to generate specific amplicons by digital PCR. The nucleic acid loci to be targeted and the species of or panel of sequence-specific primers to be included in she reactions are determined or selected prior to nucleic acid analysis.

Clinically, it has been shown to be useful for the detection of loss of heterozygosity (LOH) in tumor DNA samples (Zhou, W. et al. 2002 Lancet 359, 219-225). For the analysis of digital PCR results, sequential probability ratio testing (SPRT) has been adopted by previous studies to classify the experimental results as being suggestive of the presence of LOH in a sample or not (El Karoui et al. 2006 Stat Med 25, 3124-3133).

In methods used in the previous studies, the amount of data collected from the digital PCR is quite low. Thus, the accuracy can be compromised due to the small number of data points and typical statistical fluctuations.

It is therefore desirable that noninvasive tests have high sensitivity and specificity to minimize false negatives and false positives, respectively. However, fetal DNA is present in low absolute concentration and represent a minor portion of all DNA sequences in maternal plasma and serum. It is therefore also desirable to have methods that allow the noninvasive detection of fetal chromosomal aneuploidy by maximizing the amount of genetic information that could be inferred from the limited amount of fetal nucleic acids which exist as a minor population in a biological sample containing maternal background nucleic acids.

BRIEF SUMMARY

Embodiments of this invention provide methods, systems, and apparatus for determining whether a nucleic acid sequence imbalance (e.g., chromosome imbalance) exists within a biological sample obtained from a pregnant female. This determination may be done by using a parameter of an amount of a clinically-relevant chromosomal region in relation to other non-clinically-relevant chromosomal regions (background regions) within a biological sample. In one aspect, an amount of chromosomes is determined from a sequencing of nucleic acid molecules in a maternal sample, such as urine, plasma, serum, and other suitable biological samples. Nucleic acid molecules of the biological sample are sequenced, such that a fraction of the genome is sequenced. One or more cutoff values are chosen for determining whether a change compared to a reference quantity exists (i.e. an imbalance), for example, with regards to the ratio of amounts of two chromosomal regions (or sets of regions).

According to one exemplary embodiment, a biological sample received from a pregnant female is analyzed to perform a prenatal diagnosis of a fetal chromosomal aneuploidy. The biological sample includes nucleic acid molecules. A portion of the nucleic acid molecules contained in the biological sample are sequenced. In one aspect, the amount of genetic information obtained is sufficient for accurate diagnosis yet not overly excessive so as to contain costs and the amount of input biological sample required.

Based on the sequencing, a first amount of a first chromosome is determined from sequences identified as originating from the first chromosome. A second amount of one or more second chromosomes is determined from sequences identified as originating from one of the second chromosomes. A parameter from the first amount and the second amount is then compared to one or more cutoff values. Based on the comparison, a classification of whether a fetal chromosomal aneuploidy exists for the first chromosome is determined. The sequencing advantageously maximizes the amount of genetic information that could be inferred from the limited amount of fetal nucleic acids which exist as a minor population in a biological sample containing maternal background nucleic acids.

According to one exemplary embodiment, a biological sample received from a pregnant female is analyzed to perform a prenatal diagnosis of a fetal chromosomal aneuploidy. The biological sample includes nucleic acid molecules. A percentage of fetal DNA in the biological sample is identified. A number N of sequences to be analyzed based on a desired accuracy is calculated based on the percentage. At least N of the nucleic acid molecules contained in the biological sample are randomly sequenced.

Based on the random sequencing, a first amount of a first chromosome is determined from sequences identified as originating from the first chromosome. A second amount of one or more second chromosomes is determined from sequences identified as originating from one of the second chromosomes. A parameter from the first amount and the second amount is then compared to one or more cutoff values. Based on the comparison, a classification of whether a fetal chromosomal aneuploidy exists for the first chromosome is determined. The random sequencing advantageously maximizes the amount of genetic information that could be inferred from the limited amount of fetal nucleic acids which exist as a minor population in a biological sample containing maternal background nucleic acids.

Other embodiments of the invention are directed to systems and computer readable media associated with methods described herein.

A better understanding of the nature and advantages of the present invention may be gained with reference to the following detailed description and the accompanying drawings.

BRIEF DESCRIPTION OF THE DRAWINGS

FIG. 6 shows a table of a portion of human genome that was analyzed according to an embodiment of the present invention. T21 denote a sample obtained from a pregnancy involving a trisomy 21 fetus.

Figure 7:
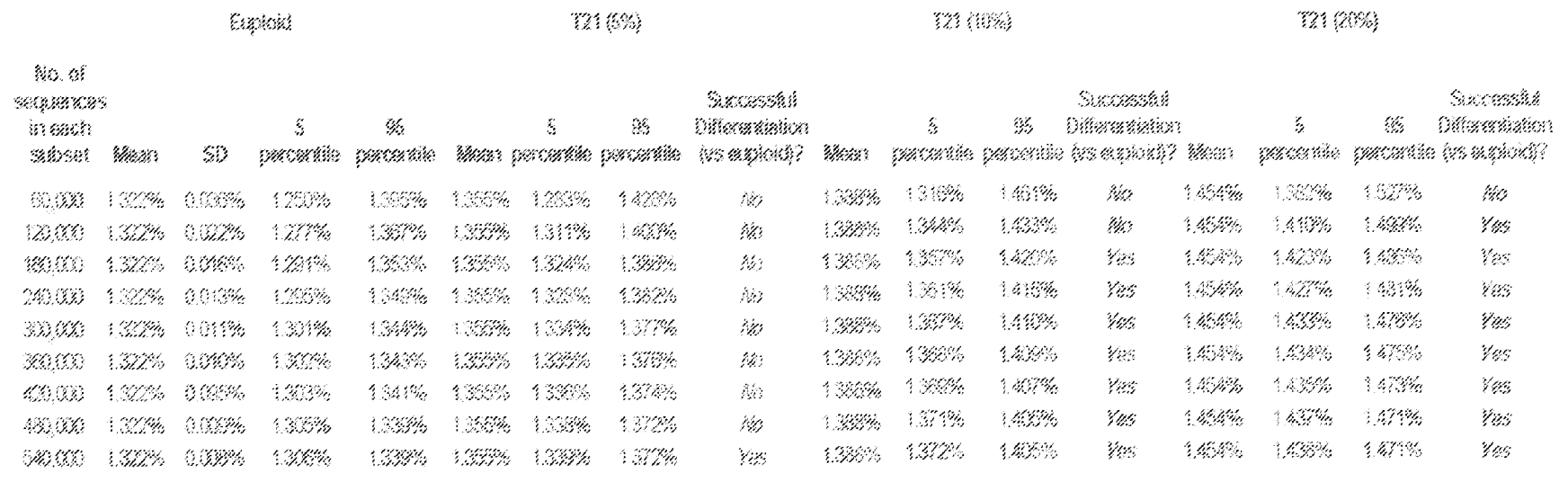

FIG. 7 shows a table of a number of sequences required to differentiate euploid from trisomy 21 fetuses according to an embodiment of the present invention.

FIG. 8A shows a table of top ten starting positions of sequenced tags aligned to chromosome 21 according to an embodiment of the present invention.

FIG. 8B shows a table of top ten starting positions of sequenced tags aligned to chromosome 22 according to an embodiment of the present invention.

DEFINITIONS

Figure 1:
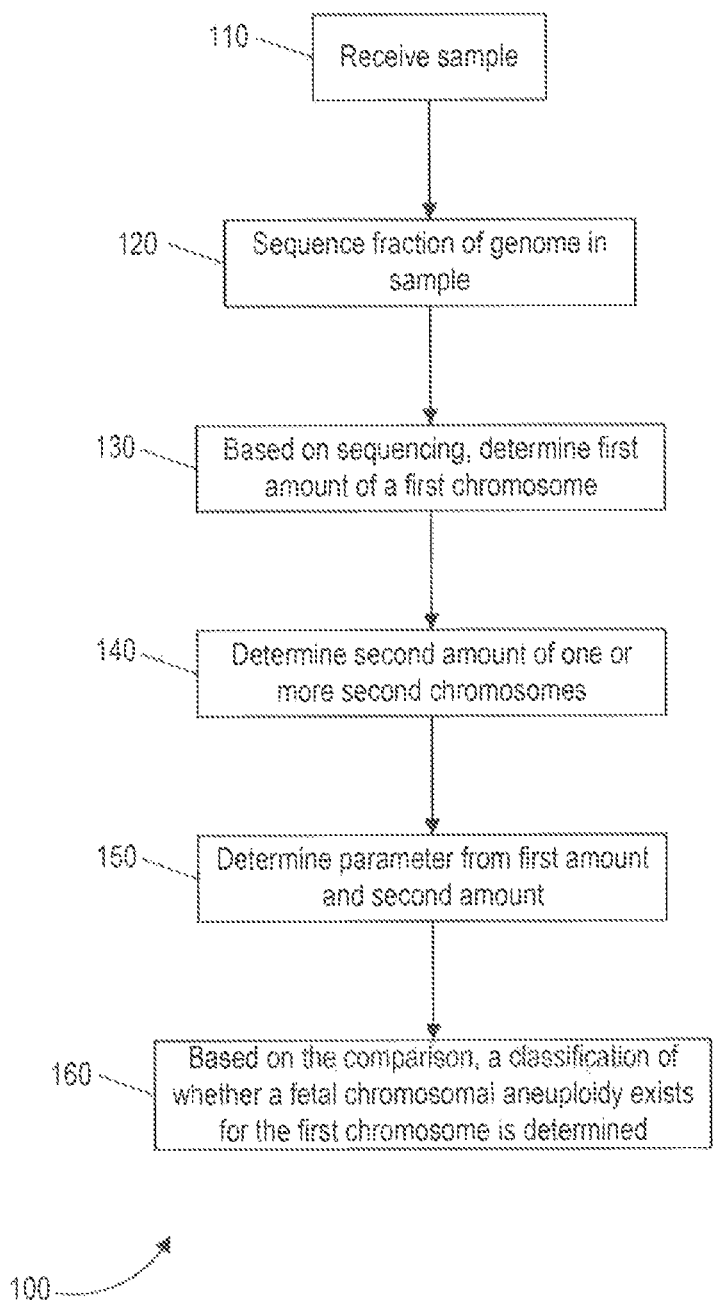
FIG. 1 is a flowchart of a method 100 for performing prenatal diagnosis of a fetal chromosomal aneuploidy in a biological sample obtained from a pregnant female subject according to an embodiment of the present invention.

The term "biological sample" as used herein refers to any sample that is taken from a subject (e.g., a human, such as a pregnant woman) and contains one or more nucleic acid molecule(s) of interest.

The term "nucleic acid" or "polynucleotide" refers to a deoxyribonucleic acid (DNA) or ribonucleic acid (RNA) and a polymer thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene cDNA, mRNA, small noncoding RNA, micro RNA (miRNA), Piwi-interacting RNA, and short hairpin RNA (shRNA) encoded by a gene or locus.

The term "gene" means the segment of DNA involved in producing a polypeptide chain. It may include regions preceding and following the coding region (leader and trailer) as well as intervening sequences (introns) between individual coding segments (exons).

The term "reaction" as used herein refers to any process involving a chemical, enzymatic, or physical action that is indicative of the presence or absence of a particular polynucleotide sequence of interest. An example of a "reaction" is an amplification reaction such as a polymerase chain reaction (PCR). Another example of a "reaction" is a sequencing reaction, either by synthesis or by ligation. An "informative reaction" is one that indicates the presence of one or more particular polynucleotide sequence of interest, and in one case where only one sequence of interest is present. The term "well" as used herein refers to a reaction at a predetermined location within a confined structure, e.g., a well-shaped vial, cell, or chamber in a PCR array.

The term "clinically relevant nucleic acid sequence" as used herein can refer to a polynucleotide sequence corresponding to a segment of a larger genomic sequence whose potential imbalance is being tested or to the larger genomic sequence itself. One example is the sequence of chromosome 21. Other examples include chromosome 18, 13, X and Y. Yet other examples include mutated genetic sequences or genetic polymorphisms or copy number variations that a fetus may inherit from one or both of its parents. Yet other examples include sequences which are mutated, deleted, or amplified in a malignant tumor, e.g. sequences in which loss of heterozygosity or gene duplication occur. In some embodiments, multiple clinically relevant nucleic acid sequences, or equivalently multiple makers of the clinically relevant nucleic acid sequence, can be used to provide data for detecting the imbalance. For instance, data from five non-consecutive sequences on chromosome 21 can be used in an additive fashion for the determination of possible chromosomal 21 imbalance, effectively reducing the need of sample volume to 1/5.

The term "background nucleic acid sequence" as used herein refers to a nucleic acid sequence whose normal ratio to the clinically relevant nucleic acid sequence is known, for instance a 1-to-1 ratio. As one example, the background nucleic acid sequence and the clinically relevant nucleic acid sequence are two alleles from the same chromosome that are distinct due to heterozygosity. In another example, the background nucleic acid sequence is one allele that is heterozygous to another allele that is the clinically relevant nucleic acid sequence. Moreover, some of each of the background nucleic acid sequence and the clinically relevant nucleic acid sequence may come from different individuals.

The term "reference nucleic acid sequence" as used herein refers to a nucleic acid sequence whose average concentration per reaction is known or equivalently has been measured.

The term "overrepresented nucleic acid sequence" as used herein refers to the nucleic acid sequence among two sequences of interest (e.g., a clinically relevant sequence and a background sequence) that is in more abundance than the other sequence in a biological sample.

The term "based on" as used herein means "based at least in part on" and refers to one value (or result) being used in the determination of another value, such as occurs in the relationship of an input of a method and the output of that method. The term "derive" as used herein also refers to the relationship of an input of a method and the output of that method, such as occurs when the derivation is the calculation of a formula.

The term "quantitative data" as used herein means data that are obtained from one or more reactions and that provide one or more numerical values. For example, the number of wells that show a fluorescent marker for a particular sequence would be quantitative data.

The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter.

The term "cutoff value" as used herein means a numerical value whose value is used to arbitrate between two or more states (e.g. diseased and non-diseased) of classification for a biological sample. For example, if a parameter is greater than the cutoff value, a first classification of the quantitative data is made (e.g. diseased state); or if the parameter is less than the cutoff value, a different classification of the quantitative data is made (e.g. non-diseased state).

The term "imbalance" as used herein means any significant deviation as defined by at least one cutoff value in a quantity of the clinically relevant nucleic acid sequence from a reference quantity. For example, the reference quantity could be a ratio of 3/5, and thus an imbalance would occur if the measured ratio is 1:1.

The term "chromosomal aneuploidy" as used herein, means a variation in the quantitative amount of a chromosome from that of a diploid genome. The variation may be a gain or a loss. It may involve the whole of one chromosome or a region of a chromosome.

The term, "random sequencing" as used herein refers to sequencing whereby the nucleic acid fragments sequenced have not been specifically identified or targeted before the sequencing procedure. Sequence-specific primers to target specific gene loci are not required. The pools of nucleic acids sequenced vary from sample to sample and even from analysis to analysis for the same sample. The identities of the sequenced nucleic acids are only revealed from the sequencing output generated. In some embodiments of the present invention, the random sequencing may be preceded by procedures to enrich a biological sample with particular populations of nucleic acid molecules sharing certain common features. In one embodiment, each of the fragments in the biological sample have an equal probability of being sequenced.

The term "fraction of the human genome" or "portion of the human genome" as used herein refers to less than 100% of the nucleotide sequences in the human genome which comprises of some 3 billion basepairs of nucleotides. In the context of sequencing, it refers to less than 1-fold coverage of the nucleotide sequences in the human genome. The term may be expressed as a percentage or absolute number of nucleotides/basepairs. As an example of use, the term may be used to refer to the actual amount of sequencing performed. Embodiments may determine the required minimal value for the sequenced fraction of the human genome to obtain an accurate diagnosis. As another example of use, the term may refer to the amount of sequenced data used for deriving a parameter or amount for disease classification.

The term "sequenced tag" as used herein refers to string of nucleotides sequenced from any part or all of a nucleic acid molecule. For example, a sequenced tag may be a short string of nucleotides sequenced from a nucleic acid fragment, a short string of nucleotides at both ends of a nucleic acid fragment, or the sequencing of the entire nucleic acid fragment that exists in the biological sample. A nucleic acid fragment is any part of a larger nucleic acid molecule. A fragment (e.g. a gene) may exist separately (i.e. not connected) to the other parts of the larger nucleic acid molecule.

DETAILED DESCRIPTION

Embodiments of this invention provide methods, systems, and apparatus for determining whether an increase or decrease (diseased state) of a clinically-relevant chromosomal region exists compared to a non-diseased state. This determination may be done by using a parameter of an amount of a clinically-relevant chromosomal region in relation to other non-clinically-relevant chromosomal regions (background regions) within a biological sample. Nucleic acid molecules of the biological sample are sequenced, such that a fraction of the genome is sequenced, and the amount may be determined from results of the sequencing. One or more cutoff values are chosen for determining whether a change compared to a reference quantity exists (i.e. an imbalance), for example, with regards to the ratio of amounts of two chromosomal regions (or sets of regions).

The change detected in the reference quantity may be any deviation (upwards or downwards) in the relation of the clinically-relevant nucleic acid sequence to the other non-clinically-relevant sequences. Thus, the reference state may be any ratio or other quantity (e.g. other than a 1-1 correspondence), and a measured state signifying a change may be any ratio or other quantity that differs from the reference quantity as determined by the one or more cutoff values.

The clinically relevant chromosomal region (also called a clinically relevant nucleic acid sequence) and the background nucleic acid sequence may come from a first type of cells and from one or more second types of cells. For example, fetal nucleic acid sequences originating from fetal/placental cells are present in a biological sample, such as maternal plasma, which contains a background of maternal nucleic acid sequences originating from maternal cells. In one embodiment, the cutoff value is determined based at least in part on a percentage of the first type of cells in a biological sample. Note the percentage of fetal sequences in a sample may be determined by any fetal-derived loci and not limited to measuring the clinically-relevant nucleic acid sequences. In another embodiment, the cutoff value is determined at least in part on the percentage of tumor sequences in a biological sample, such as plasma, serum, saliva or urine, which contains a background of nucleic acid sequences derived from the non-malignant cells within the body.

I. General Method

FIG. 1 is a flowchart of a method 100 for performing prenatal diagnosis of a fetal chromosomal aneuploidy in a biological sample obtained from a pregnant female subject according to an embodiment of the present invention.

In step 110, a biological sample from the pregnant female is received. The biological sample may be plasma, urine, serum, or any other suitable sample. The sample contains nucleic acid molecules from the fetus and the pregnant female. For example, the nucleic acid molecules may be fragments from chromosomes.

In step 120, at least a portion of a plurality of the nucleic acid molecules contained in the biological sample are sequenced. The portion sequenced represents a fraction of the human genome. In one embodiment, the nucleic acid molecules are fragments of respective chromosomes. One end (e.g. 35 basepairs (bp)), both ends, or the entire fragment may be sequenced. All of the nucleic acid molecules in the sample may be sequenced, or just a subset may be sequenced. This subset may be randomly chosen, as will be described in more detail later.

In one embodiment, the sequencing is done using massively parallel sequencing. Massively parallel sequencing, such as that achievable on the 454 platform (Roche) (Margulies, M. et al. 2005 *Nature* 437, 376-380), Illumina Genome Analyzer (or Solexa platform) or SOLiD System (Applied Biosystems) or the Helicos True Single Molecule DNA sequencing technology (Harris T D et al. 2008 Science, 320, 106-109), the single molecule, real-time (SMRT™) technology of Pacific Biosciences, and nanopore sequencing (Soni G V and Meller A, 2007 Clin Chem 53: 1996-2001), allow the sequencing of many nucleic acid molecules isolated from a specimen at high orders of multiplexing in a parallel fashion (Dear Brief Funct Genomic Proteomic 2003; 1: 397-416). Each of these platforms sequences clonally expanded or even non-amplified single molecules of nucleic acid fragments.

As a high number of sequencing reads, in the order of hundred thousands to millions or even possibly hundreds of millions or billions, are generated from each sample in each run, the resultant sequenced reads form a representative profile of the mix of nucleic acid species in the original specimen. For example, the haplotype, trascriptome and methylation profiles of the sequenced reads resemble those of the original specimen (Brenner et al Nat Biotech 2000; 18: 630-634; Taylor et al Cancer Res 2007; 67: 8511-8518). Due to the large sampling of sequences from each specimen, the number of identical sequences, such as that generated from the sequencing of a nucleic acid pool at several folds of coverage or high redundancy, is also a good quantitative representation of the count of a particular nucleic acid species or locos in the original sample.

In step 130, based on the sequencing (e.g. data from the sequencing), a first amount of a first chromosome (e.g. the clinically relevant chromosome) is determined. The first amount is determined from sequences identified as originating from the first chromosome. For example, a bioinformatics procedure may then be used to locate each of these DNA sequences to the human genome. It is possible that a proportion of such sequences will be discarded from subsequent analysis because they are present in the repeat regions of the human genome, or in regions subjected to inter-individual variations, e.g. copy number variations. An amount of the chromosome of interest and of one or more other chromosomes may thus be determined.

In step 140, based on the sequencing, a second amount of one or more second chromosomes is determined from sequences identified as originating from one of the second chromosomes. In one embodiment, the second chromosomes are all of the other chromosomes besides the first one (i.e. the one being tested). In another embodiment, the second chromosome is just a single other chromosome.

There are a number of ways of determining the amounts of the chromosomes, including but not limited to counting the number of sequenced tags, the number of sequenced nucleotides (basepairs) or the accumulated lengths of sequenced nucleotides (basepairs) originating from particular chromosome(s) or chromosomal regions.

In another embodiment, rules may be imposed on the results of the sequencing to determine what gets counted. In one aspect, an amount may be obtained based on a proportion of the sequenced output. For example, sequencing output corresponding to nucleic acid fragments of a specified size range could be selected after the bioinformatics analysis. Examples of the size ranges are about <300 bp, <200 bp or <100 bp.

In step 150, a parameter is determined from the first amount and the second amount. The parameter may be, for example, a simple ratio of the first amount to the second amount, or the first amount to the second amount plus the first amount. In one aspect, each amount could be an argument to a function or separate functions, where a ratio may be then taken of these separate functions. One skilled in the art will appreciate the number of different suitable parameters.

In one embodiment, a parameter (e.g. a fractional representation) of a chromosome potentially involved in a chromosomal aneuploidy, e.g. chromosome 21 or chromosome 18 or chromosome 13, may then be calculated from the results of the bioinformatics procedure. The fractional representation may be obtained based on an amount of all of the sequences (e.g. some measure of all of the chromosomes including the clinically-relevant chromosome) or a particular subset of chromosomes (e.g. just one other chromosome than the one being tested.)

In step 150, the parameter is compared to one or more cutoff values. The cutoff values may be determined from any number of suitable ways. Such ways include Bayesian-type likelihood method, sequential probability ratio testing (SPRT), false discovery, confidence interval, receiver operating characteristic (ROC). Examples of applications of these methods and sample-specific methods are described in concurrently filed application "DETERMINING A NUCLEIC ACID SEQUENCE IMBALANCE," Ser. No. 12/178,116 which is incorporated by reference.

In one embodiment, the parameter (e.g. the fractional representation of the clinically relevant chromosome) is then compared to a reference range established in pregnancies involving normal (i.e. euploid) fetuses. It is possible that in some variants of the procedure, the reference range (i.e. the cutoff values) would be adjusted in accordance with the fractional concentration of fetal DNA (f) in a particular maternal plasma sample. The value of f can be determined from the sequencing dataset, e.g. using sequences mappable to the Y chromosome if the fetus is male. The value of f may also be determined in a separate analysis, e.g. using fetal epigenetic markers (Chan K C A et al 2006 Clin Chem 52, 2211-8) or from the analysis of single nucleotide polymorphisms.

In step 160, based on the comparison, a classification of whether a fetal chromosomal aneuploidy exists for the first chromosome is determined. In one embodiment, the classification is a definitive yes or no. In another embodiment, a classification may be unclassifiable or uncertain. In yet another embodiment, the classification may be a score that is to be interpreted at a later date, for example, by a doctor.

II. Sequencing, Aligning, and Determining Amounts

As mentioned above, only a fraction of the genome is sequenced. In one aspect, even when a pool of nucleic acids in a specimen is sequenced at <100% genomic coverage instead of at several folds of coverage, and among the proportion of captured nucleic acid molecules, most of each nucleic acid species is only sequenced once. Also, dosage imbalance of a particular chromosome or chromosomal regions can be quantitatively determined. In other words, the dosage imbalance of the chromosome or chromosomal regions is inferred from, the percentage representation of the said locus among other mappable sequenced tags of the specimen.

This is contrasted from situations where the same pool of nucleic acids is sequenced multiple times to achieve high redundancy or several folds of coverage whereby each nucleic acid species is sequenced multiple times. In such situations, the number of times a particular nucleic acid species have been sequenced relative to that of another nucleic acid species correlate with their relative concentrations in the original sample. The sequencing cost increases with the number of fold coverage required to achieve accurate representation of the nucleic acid species.

In one example, a proportion of such sequences would be from the chromosome involved in an aneuploidy such as chromosome 21 in this illustrative example. Yet other sequences from such a sequencing exercise would be derived from the other chromosomes. By taking into account of the relative size of chromosome 21 compared with the other chromosomes, one could obtain a normalized frequency, within a reference range, of chromosome 21-specific sequences from such a sequencing exercise. If the fetus has trisomy 21, then the normalized frequency of chromosome 21-derived sequences from such a sequencing exercise will increase, thus allowing the detection of trisomy 21. The degree of change in the normalized frequency will be dependent on the fractional concentration of fetal nucleic acids in the analyzed sample.

In one embodiment, we used the Illumina Genome Analyzer for single-end sequencing of human genomic DNA and human plasma DNA samples. The Illumina Genome Analyzer sequences clonally-expanded single DNA molecules captured on a solid surface termed a flow cell. Each flow cell has 8 lanes for the sequencing of 8 individual specimens or pools of specimens. Each lane is capable of generating ~200 Mb of sequence which is only a fraction of the 3 billion basepairs of sequences in the human genome. Each genomic DNA or plasma DNA sample was sequenced using one lane of a flow cell. The short sequence tags generated were aligned to the human reference genome sequence and the chromosomal origin was noted. The total number of individual sequenced tags aligned to each chromosome were tabulated and compared with the relative size of each chromosome as expected from the reference human genome or non-disease representative specimens. Chromosome gains or losses were then identified.

The described approach is only one exemplification of the presently described gene/chromosome dosage strategy. Alternatively, paired end sequencing could be performed. Instead of comparing the length of the sequenced fragments from that expected in the reference genome as described by Campbell et al (Nat Genet 2008; 40: 722-729), the number of aligned sequenced tags were counted and sorted according to chromosomal location. Gains or losses of chromosomal regions or whole chromosomes were determined by comparing the tag counts with the expected chromosome size in the reference genome or that of a non-disease representative specimen. As paired end sequencing allows one to deduce the size of the original nucleic acid fragment, one example is to focus on the counting of the number of paired sequenced tags corresponding to nucleic acid fragments of a specified size, such as <300 bp, <200 bp or <100 bp.

In another embodiment, the fraction of the nucleic acid pool that is sequenced in a run is further sub-selected prior to sequencing. For example, hybridization based techniques such as oligonucleotide array could be used to first sub-select for nucleic acid sequences from certain chromosomes, e.g. a potentially aneuploid chromosome and other chromosome(s) not involved in the aneuploidy rested. Another example is that a certain sub-population of nucleic acid sequences from the sample pool is sub-selected or enriched prior to sequencing. For example, as discussed above, it has been reported that fetal DNA molecules in maternal plasma are comprised of shorter fragments than the maternal background DNA molecules (Chan et al Clin Chem 2004; 50: 88-92). Thus, one may use one or more methods known to those of skill in the art to fractionate the nucleic acid sequences in the sample according to molecule size, e.g. by gel electrophoresis or size exclusion columns or by microfluidics-based approach. Yet, alternatively, in the example of analyzing cell-free fetal DNA in maternal plasma, the fetal nucleic acid portion could be enriched by a method that suppresses the maternal background, such as by the addition of formaldehyde (Dhallan et al JAMA 2004; 291: 1114-9). In one embodiment, a portion or subset of the pre-selected pool of nucleic acids is sequenced randomly.

Other single molecule sequencing strategies such as that by the Roche 454 platform, the Applied Biosystems SOLiD platform, the the Helicos True Single Molecule DNA sequencing technology, the single molecule, real-time (SMRT™) technology of Pacific Biosciences, and nanopore sequencing could similarly be used in this application.

III. Determining Amounts of Chromosomes from Sequencing Output

After the massively parallel sequencing, bioinformatics analysis was performed to locate the chromosomal origin of the sequenced tags. After this procedure, tags identified as originating from the potentially aneuploid chromosome, i.e. chromosome 21 in this study, are compared quantitatively to all of the sequenced tags or tags originating from one of more chromosomes not involved in the aneuploidy. The relationship between the sequencing output from chromosome 21 and other non-21 chromosomes for a test specimen is compared with cut-off values derived with methods described in the above section to determine if the specimen was obtained from a pregnancy involving a euploid or trisomy 21 fetus.

A number of different amounts include but not limited to the following could be derived from the sequenced tags. For example, the number of sequenced tags, i.e. absolute count, aligned to a particular chromosome could be compared to the absolute count of sequenced tags aligned to other chromosomes. Alternatively, the fractional count of the amount of sequenced tags from chromosome 21 with reference to all or some other sequenced tags could be compared to that of other non-aneuploid chromosomes. In the present experiment, because 36 bp were sequenced from each DNA fragment, the number of nucleotides sequenced from a particular chromosome could easily be derived from 36 bp multiplied by the sequenced tag count.

Furthermore, as each maternal plasma specimen was only sequenced using one flow cell which could only sequence a fraction of the human genome, by statistics, most of the maternal plasma DNA fragment species would only each have been sequenced to generate one sequenced tag count. In other words, the nucleic acid fragments present in the maternal plasma specimen were sequenced at less than 1-fold coverage. Thus, the total number of sequenced nucleotides for any particular chromosome would mostly correspond to the amount, proportion or length of the part of the said chromosome that has been sequenced. Hence, the quantitative determination of the representation of the potentially aneuploid chromosome could be derived from a fraction of the number or equivalent length of nucleotides sequenced from that chromosome with reference to a similarly derived quantity for other chromosomes.

IV. Enrichment for Pools of Nucleic Acids for Sequencing

As mentioned above and established in the example section below, only a portion of the human genome needs to be sequenced to differentiate trisomy 21 from euploid cases. Thus, it would be possible and cost-effective to enrich the pool of nucleic acids to be sequenced prior to random sequencing of a fraction of the enriched pool. For example, fetal DNA molecules in maternal plasma are comprised of shorter fragments than the maternal background DNA molecules (Chan et al Clin Chem 2004; 50: 88-92). Thus, one may use one or more methods known to those of skill in the art to fractionate the nucleic acid sequences in the sample according to molecule size, e.g. by gel electrophoresis or size exclusion columns or by microfluidics-based approach.

Yet, alternatively, in the example of analyzing cell-free fetal DNA in maternal plasma, the fetal nucleic acid portion could be enriched by a method that suppresses the maternal background, such as by the addition of formaldehyde (Dhallan et al JAMA 2004; 291: 1114-9). The proportion of fetal derived sequences would be enriched in the nucleic acid pool comprised of shorter fragments. According to FIG. 7, the number of sequenced tags required for differentiating euploid from trisomy 21 cases would reduce as the fractional fetal DNA concentration increases.

Alternatively, sequences originating from a potentially aneuploid chromosome and one or more chromosomes not involved in the aneuploidy could be enriched by hybridization techniques for example onto oligonucleotide microarrays. The enriched pools of nucleic acids would then be subjected to random sequencing. This would allow the reduction in sequencing costs.

V. Random Sequencing

Figure 2:
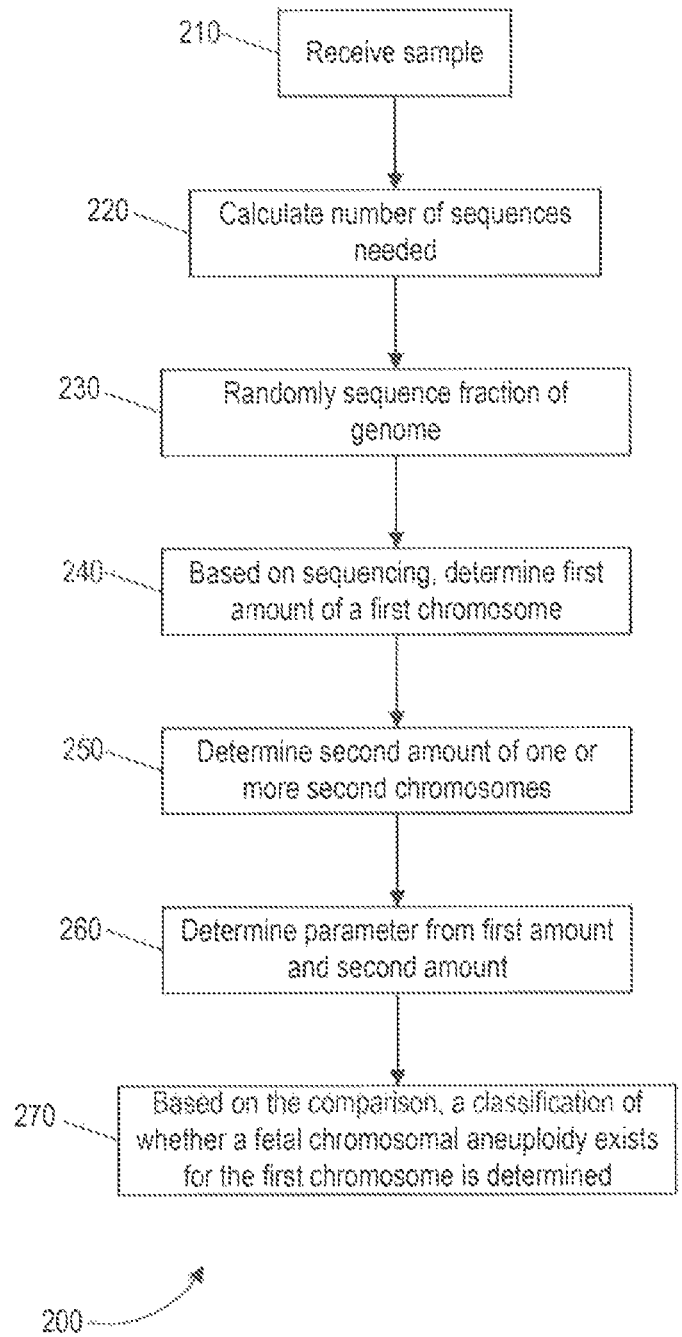
FIG. 2 is a flowchart of a method 200 for performing prenatal diagnosis of a fetal chromosomal aneuploidy using random sequencing according to an embodiment of the present invention.

FIG. 2 is a flowchart of a method 200 for performing prenatal diagnosis of a fetal chromosomal aneuploidy using random sequencing according to an embodiment of the present invention. In one aspect, for the massively parallel sequencing approach, representative data from all of the chromosomes may be generated at the same time. The origin of a particular fragment is not selected ahead of time. The sequencing is done at random and then a database search may be performed to see where a particular fragment is coming from. This is contrasted from situations when a specific fragment from chromosome 21 and another one from chromosome 1 are amplified.

In step 210, a biological sample from the pregnant female is received. In step 220, the number N of sequences to be analyzed is calculated for a desired accuracy. In one embodiment, a percentage of fetal DNA in the biological sample is first identified. This may be done by any suitable means as will be known to one skilled in the art. The identification may simply be reading a value that was measured by another entity. In this embodiment, the calculation of the number N of sequences to be analyzed is based on the percentage. For example, the number of sequences needed to be analyzed would be increased when the fetal DNA percentage drops, and could be decreased when the fetal DNA rises. The number N may be a fixed number or a relative number, such as a percentage. In another embodiment, one could sequence a number N that is known to be adequate for accurate disease diagnosis. The number N could be made sufficient even in pregnancies with fetal DNA concentrations that are at the lower end of the normal range.

In step 230, at least N of a plurality of the nucleic acid molecules contained in the biological sample are randomly sequenced. A feature of this described approach is that the nucleic acids to be sequenced are trot specifically identified or targeted before sample analysis, i.e. sequencing. Sequence-specific primers to target specific gene loci are not needed for sequencing. The pools of nucleic acids sequenced vary from sample to sample and even from analysis to analysis for the same sample. Furthermore, from the below descriptions (FIG. 6), the amount of sequencing output required for case diagnosis could vary between the tested specimens and the reference population. These aspects are in marked contrast to most molecular diagnostic approaches, such as those based on fluorescence in situ hybridization, quantitative florescence PCR, quantitative real-time PCR, digital PCR, comparative genomic hybridization, microarray comparative genomic hybridization and so on, where gene loci to be targeted require prior pre-determination, thus requiring the use of locus-specific primers or probe sets or panels of such.

In one embodiment, random sequencing is performed on DNA fragments that are present in the plasma of a pregnant woman, and one obtains genomic sequences which would originally have come from either the fetus or the mother. Random sequencing involves sampling (sequencing) a random portion of the nucleic acid molecules present in the biological sample. As the sequencing is random, a different subset (fraction) of the nucleic acid molecules (and thus the genome) may be sequenced in each analysis. Embodiments will work even when this subset varies from sample to sample and from analysis to analysis, which may occur even using the same sample. Examples of the fraction are about 0.1%, 0.5%, 1%, 5%, 10%, 20%, or 30% of the genome. In other embodiments, the fraction is at least any one of these values.

The rest of the steps 240-270 may proceed in a similar manner as method 100.

VI. Post-Sequencing Selection of Pools of Sequenced Tags

As described in examples II and III below, a subset of the sequenced data is sufficient to distinguish trisomy 21 from euploid cases. The subset of sequenced data could be the proportion of sequenced tags that passed certain quality parameters. For example, in example II, sequenced tags that were uniquely aligned to the repeat-masked reference human genome were used. Alternatively, one may sequence a representative pool of nucleic acid fragments from all of the chromosomes but focus on the comparison between data relevant to the potentially aneuploid chromosome and data relevant to a number of non-aneuploid chromosomes.

Yet alternatively, a subset of the sequencing output encompassing sequenced tags generated from nucleic acid fragments corresponding to a specified size window in the original specimen could be sub-selected during the post-sequencing analysis. For example, using the Illumina Genome analyzer, one could use paired-end sequencing which refers to sequencing the two ends of nucleic acid fragments. The sequenced data from each paired-end are then aligned to the reference human genome sequence. The distance or number of nucleotides spanning between the two ends could then be deduced. The whole length of the original nucleic acid fragment could also be deduced. Alternatively, sequencing platforms such as the 454 platform and possibly some single molecule sequencing techniques are able to sequence the full length of short nucleic acid fragments, for example 200 bp. In this manner, the actual length of the nucleic acid fragment would be immediately known from the sequenced data.

Such paired-end analysis is also possible using other sequencing platforms, e.g. the Applied Biosystems SOLiD system. For the Roche 454 platform, because of its increased read length compared with other massively parallel sequencing systems, it is also possible to determine the length of a fragment from its complete sequence.

The advantage of focusing the data analysis on the subset of sequenced tags corresponding to short nucleic acid fragments in the original maternal plasma specimen because the dataset would effectively be enriched with DNA sequences derived from the fetus. This is because the fetal DNA molecules in maternal plasma are comprised of shorter fragments than the maternal background DNA molecules (Chan et al Clin Chem 2004; 50: 88-92). According to FIG. 7, the number of sequenced tags required for differentiating euploid from trisomy 21 cases would reduce as the fractional fetal DNA concentration increases.

The post-sequencing selection of subsets of nucleic acid pools is different from other nucleic acid enrichment strategies which are performed prior to specimen analysis, such as the use gel electrophoresis or size exclusion columns for the selection of nucleic acids of particular sizes, which require the physical separation of the enriched pool from the background pool of nucleic acids. The physical procedures would introduce more experimental steps and may be prone to problems such as contamination. The post-sequencing in silico selection of subsets of sequencing output would also allow one to vary the selection depending on the sensitivity and specificity required for disease determination.

The bioinformatics, computational and statistical approaches used to determine if a maternal plasma specimen is obtained from a pregnant woman conceived with a trisomy 21 or euploid fetus could be compiled into a computer program product used to determine parameters from the sequencing output. The operation of the computer program would involve the determining of a quantitative amount from the potentially aneuploid chromosome as well as amount(s) from one or more of the other chromosomes. A parameter would be determined and compared with appropriate cut-off values to determine if a fetal chromosomal aneuploidy exists for the potentially aneuploid chromosome.

EXAMPLES

The following examples are offered to illustrate, but not to limit the claimed invention.

I. Prenatal Diagnosis of Fetal Trisomy 21

Eight pregnant women were recruited for the study. All of the pregnant women were in the $1^{st}$ or $2^{nd}$ trimester of gestation and had a singleton pregnancy. Four of them were each carrying a fetus with trisomy 21 and the other four were each carrying a euploid fetus. Twenty milliliters of peripheral venous blood was collected from each subject. Maternal plasma was harvested after centrifugation at 1600×g for 10 minutes and further centrifuged at 16000×g for 10 minutes. DNA was then extracted from 5-10 mL of each plasma sample. The maternal plasma DNA was then used for massively parallel sequencing by the Illumina Genome Analyzer according to manufacturer's instructions. The technicians performing the sequencing were blinded from the fetal diagnoses during the sequencing and sequence data analysis.

Briefly, approximately 50 ng of maternal plasma DNA was used for DNA library preparation. It is possible to start with lesser amounts such as 15 ng or 10 ng of maternal plasma DNA. Maternal plasma DNA fragments were blunt-ended, ligated to Solexa adaptors and fragments of 150-300 bp were selected by gel purification. Alternatively, blunt-ended and adaptor-ligated maternal plasma DNA fragments could be passed through columns (e.g. AMPure, Agencourt) to remove unligated adaptors without size-selection before cluster generation. The adaptor-ligated DNA was hybridized to the surface of flow cells, and DNA clusters were generated using the Illumina cluster station, followed by 36 cycles of sequencing on the Illumina Genome Analyzer. DNA from each maternal plasma specimen was sequenced by one flow cell. Sequenced reads were compiled using Solexa Analysis Pipeline. All reads were then aligned to the repeat-masked reference human genomic sequence, NCBI 36 assembly (GenBank accession numbers: NC_000001 to NC_000024), using the Eland application.

In this study, to reduce the complexity of the data analysis, only sequences that have been mapped to a unique location in the repeat-masked human genome reference are further considered. Other subsets of or the entire set of the sequenced data could alternatively be used. The total number of uniquely mappable sequences for each specimen was counted. The number of sequences uniquely aligned to chromosome 21 was expressed as a proportion to the total count of aligned sequences for each specimen. As maternal plasma contains fetal DNA among a background of DNA of maternal origin, the trisomy 21 fetus would contribute extra sequenced tags originating from chromosome 21 due to the presence of an extra copy of chromosome 21 in the fetal genome. Hence, the percentage of chromosome 21 sequences in maternal plasma from a pregnancy carrying a trisomy 21 fetus would be higher than that from a pregnancy with a diploid fetus. The analysis does not require the targeting of fetal-specific sequences. It also does not require the prior physical separation of fetal from maternal nucleic acids. It also does not require the need to distinguish or identify fetal from maternal sequences after sequencing.

Figure 3A:
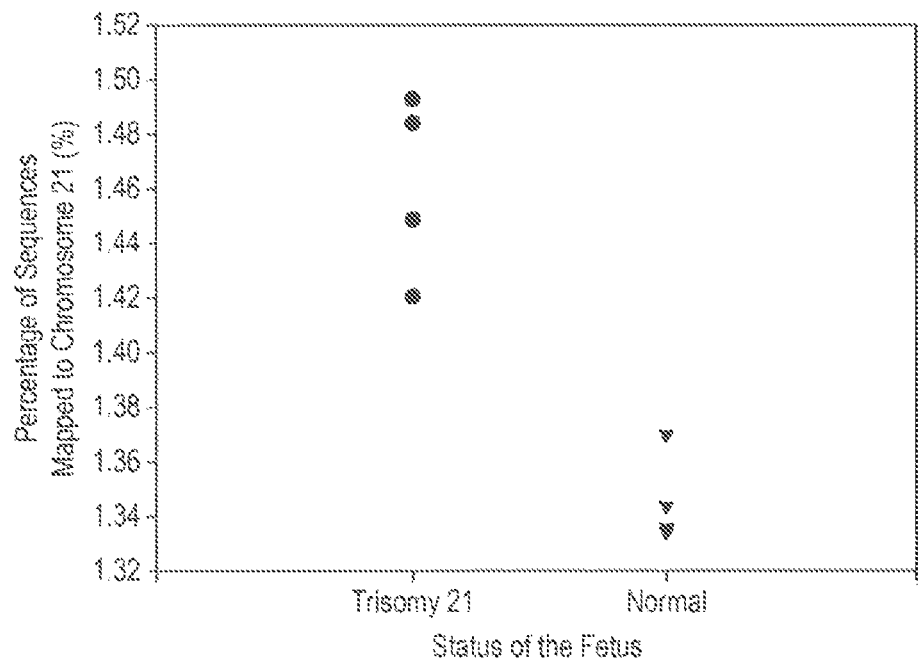
FIG. 3A shows a plot of percentage representation of chromosome 21 sequences in maternal plasma samples involving trisomy 21 or euploid fetuses according to an embodiment of the present invention.

FIG. 3A shows the percentage of sequences mapped to chromosome 21 (percentage representation of chromosome 21) for each of the 8 maternal plasma DNA samples. The percentage representation of chromosome 21 was significantly higher in maternal plasma of trisomy 21 pregnancies than in that of euploid pregnancies. These data suggest that noninvasive prenatal diagnosis of fetal aneuploidy could be achieved by determining the percentage representation of the aneuploid chromosome compared to that of a reference population. Alternatively, the chromosome 21 over-representation could be detected by comparing the percentage representation of chromosome 21 obtained experimentally with the percentage representation of chromosome 21 sequences expected for a euploid human genome. This could be done by masking or not masking the repeat regions in the human genome.

Five of the eight pregnant women were each carrying a male fetus. The sequences mapped to the Y chromosome would be fetal-specific. The percentage of sequences mapped to the Y-chromosome was used to calculate the fractional fetal DNA concentration in the original maternal plasma specimen. Moreover, the fractional fetal DNA concentration was also determined by using microfluidics digital PCR involving the zinc finger protein, X-linked (ZFX) and zinc finger protein, Y-linked (ZFY) paralogous genes.

Figure 3B:
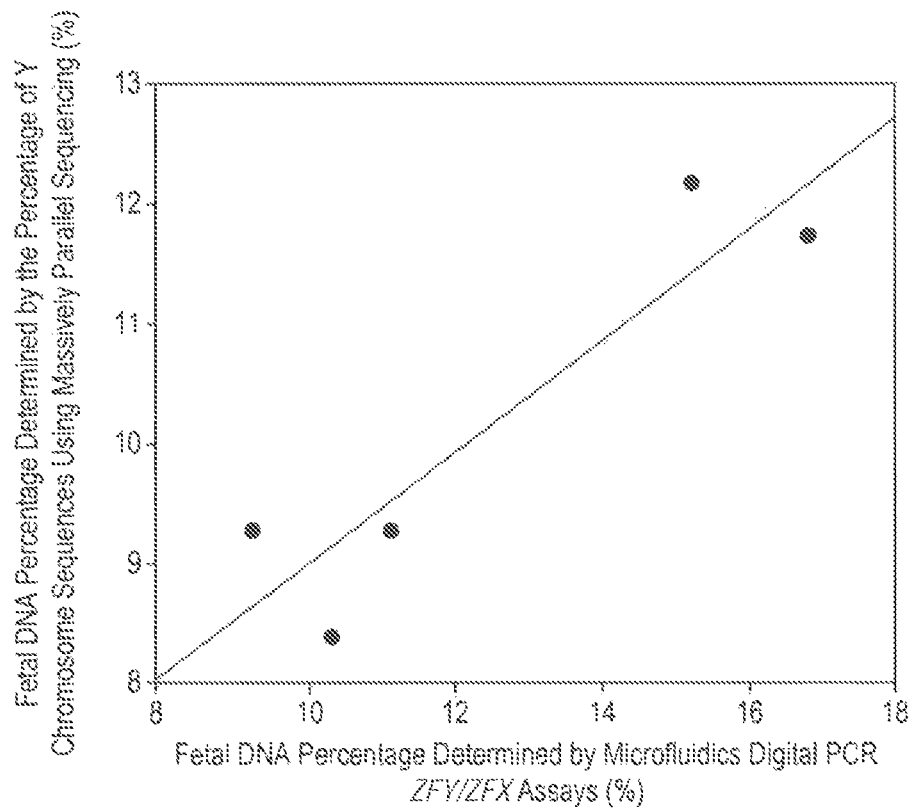
FIG. 3B shows a correlation between maternal plasma fractional fetal DNA concentrations determined by massively parallel sequencing and microfluidics digital PCR according to an embodiment of the present invention.

FIG. 3B shows the correlation of the fractional fetal DNA concentrations as inferred by the percentage representation of Y chromosome by sequencing and that determined by ZFY/ZFX microfluidics digital PCR. There was a positive correlation between the fractional fetal DNA concentrations in maternal plasma determined by these two methods. The coefficient of correlation (r) was 0.917 in the Pearson correlation analysis.

Figure 4A:
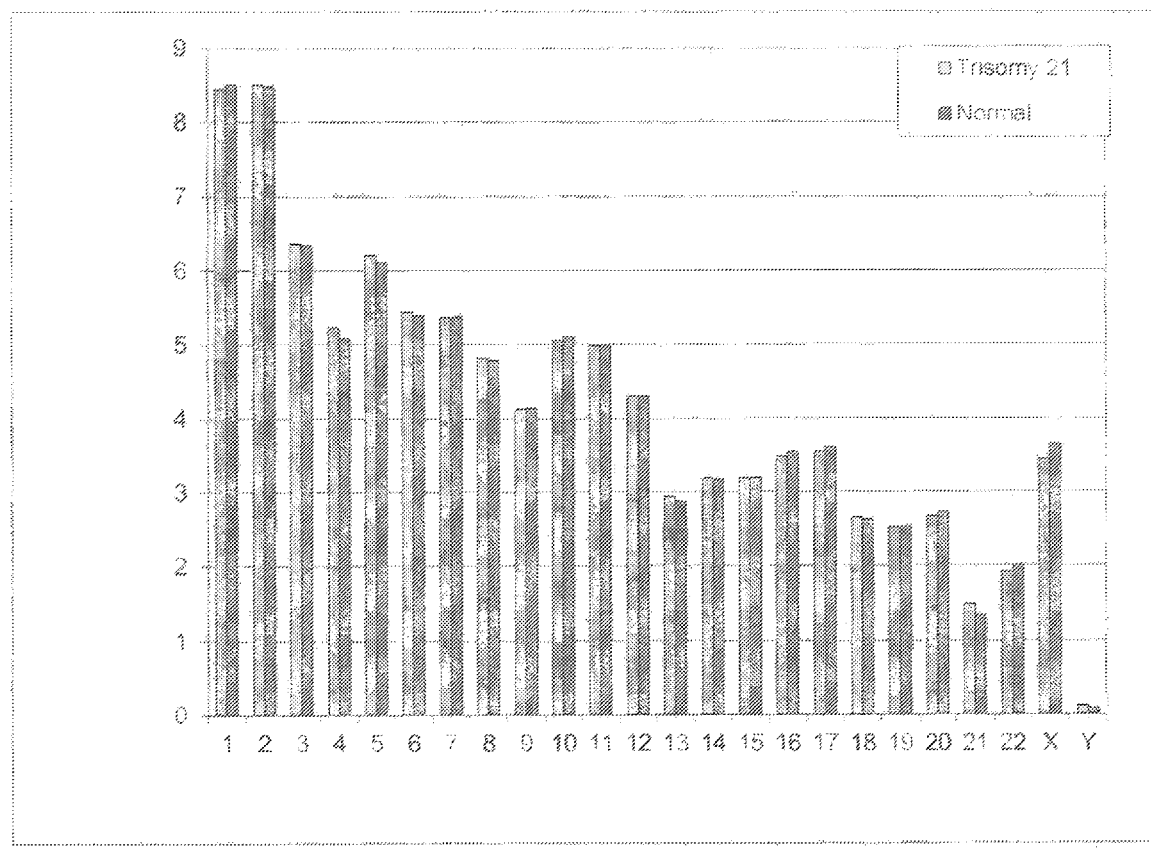
FIG. 4A shows a plot of percentage representation of aligned sequences per chromosome according to an embodiment of the present invention.

The percentages of maternal plasma DNA sequences aligned to each of the 24 chromosomes (22 autosomes and X and Y chromosomes) for two representative cases are shown in FIG. 4A. One pregnant woman was carrying a trisomy 21 fetus and the other was carrying a euploid fetus. The percentage representation of sequences mapped to chromosome 21 is higher in the pregnant woman carrying a trisomy 21 fetus when compared with the pregnant woman carrying a normal fetus.

Figure 4B:
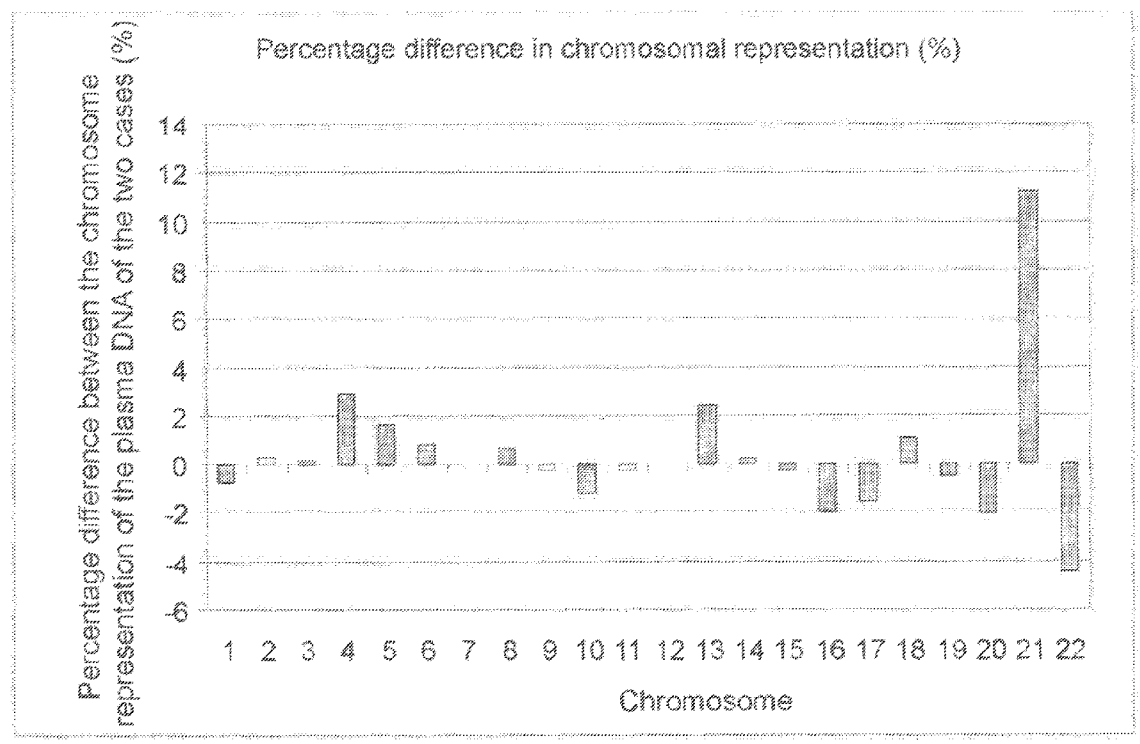
FIG. 4B shows a plot of difference (%) in percentage representation per chromosome between the trisomy 21 case and euploid case shown in FIG. 4A.

The differences (%) of the percentage representation per chromosome between the maternal plasma DNA specimens of the above two cases is shown in FIG. 4B. The percentage difference for a particular chromosome is calculated using the formula below:

$$\text{Percentage difference (\%)} = (P_{21} - P_E)/P_E \times 100\%,$$

where $P_{21}$=percentage of plasma DNA sequences aligned to the particular chromosome in the pregnant woman carrying a trisomy 21 fetus and;

$P_E$=percentage of plasma DNA sequences aligned to the particular chromosome in the pregnant woman carrying a euploid fetus.

As shown in FIG. 4B, there is an over-representation of chromosome 21 sequences by 11% in the plasma of the pregnant woman carrying a trisomy 21 fetus when compared with the pregnant woman carrying a euploid fetus. For the sequences aligned to other chromosomes, the differences between the two cases were within 5%. As the percentage representation for chromosome 21 is increased in the trisomy 21 compared with the euploid maternal plasma samples, the difference (%) could be alternatively referred as the degree of over-representation in chromosome 21 sequences, in addition to differences (%) and absolute differences between the chromosome 21 percentage representation, ratios of the counts from test and reference samples could also be calculated and would be indicative of the degree of chromosome 21 over-representation in trisomy 21 compared with euploid samples.

For the four pregnant women each carrying a euploid fetus, a mean of 1.345% of their plasma DNA sequences were aligned to chromosome 21. In the four pregnant women carrying a trisomy 21 fetus, three of their fetuses were males. The percentage representation of chromosome 21 was calculated for each of these three cases. The difference (%) in chromosome 21 percentage representation for each of these three trisomy 21 cases from the mean chromosome 21 percentage representation derived from values of the four euploid cases were determined as described above. In other words, the mean of the four cases carrying a euploid fetus was used as the reference in this calculation. The fractional fetal DNA concentrations for these three male trisomy 21 cases were inferred from their respective percentage representation of Y chromosome sequences.

Figure 5:
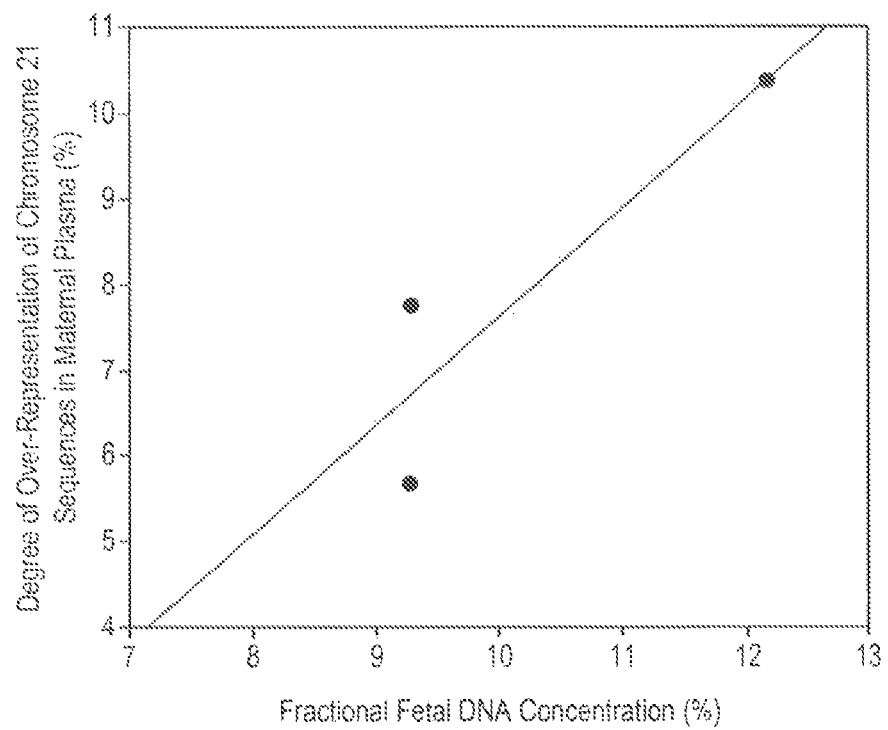
FIG. 5 shows a correlation between degree of over-representation in chromosome 21 sequences and the fractional fetal DNA concentrations in maternal plasma involving trisomy 21 fetuses according to an embodiment of the present invention.

The correlation between the degree of over-representation for chromosome 21 sequences and the fractional fetal DNA concentrations is shown in FIG. 5. There was a significant positive correlation between the two parameters. The coefficient of correlation (r) was 0.898 in the Pearson correlation analysis. These results indicate that the degree of over-representation of chromosome 21 sequences in maternal plasma is related to the fractional concentration of fetal DNA in the maternal plasma sample. Thus, cut-off values in the degree of chromosome 21 sequence over-representation relevant to the fractional fetal DNA concentrations could be determined to identify pregnancies involving trisomy 21 fetuses.

The determination of the fractional concentration of fetal DNA in maternal plasma can also be done separate to the sequencing run. For example, the Y chromosome DNA concentration could be pre-determined using real-time PCR, microfluidics PCR or mass spectrometry. For example, we have demonstrated in FIG. 3B that there is good correlation between the fetal DNA concentrations estimated based on the Y-chromosome count generated during the sequencing run and the ZFY/ZFX ratio generated external to the sequencing run. In fact, fetal DNA concentration could be determined using loci other than the Y chromosome and applicable to female fetuses. For example, Chan et al showed that fetal-derived methylated RASSF1A sequences would be detected in the plasma of pregnant women in the background of maternally derived unmethylated RASSF1A sequences (Chan et al, Clin Chem 2006; 52:2211-8). The fractional fetal DNA concentration can thus be determined by dividing the amount of methylated RASSF1A sequences by the amount of total RASSF1A (methylated and unmethylated) sequences.

It is expected that maternal plasma would be preferred over maternal serum for practicing our invention because DNA is released from the maternal blood cells during blood clotting. Thus, if serum is used, it is expected that the fractional concentration of fetal DNA will be lower in maternal plasma than maternal serum. In other words, if maternal serum is used, it is expected that more sequences would need to be generated for fetal chromosomal aneuploidy to be diagnosed, when compared with a plasma sample obtained from the same pregnant woman at the same time.

Yet another alternative way of determining the fractional concentration of fetal DNA would be through the quantification of polymorphic differences between the pregnant women and the fetus (Dhallan R, et al. 2007 *Lancet*, 369, 474-481). An example of this method would be to target polymorphic sites at which the pregnant woman is homozygous and the fetus is heterozygous. The amount of fetal-specific allele can be compared with the amount of the common allele to determine the fractional concentration of fetal DNA.

In contrast to the existing techniques for detecting chromosomal aberrations, including comparative genomic hybridization, microarray comparative genomic hybridization, quantitative real-time polymerase chain reaction, which detect and quantify one or more specific sequence(s), massively parallel sequencing is not dependent on the detection or analysis of predetermined or a predefined set of DNA sequences. A random representative fraction of DNA molecules from the specimen pool is sequenced. The number of different sequenced tags aligned to various chromosomal regions is compared between specimens containing or not containing the DNA species of interest. Chromosomal aberrations would be revealed by differences in the number (or percentage) of sequences aligned to any given chromosomal region in the specimens.

In another example the sequencing technique on plasma cell-free DNA may be used to detect the chromosomal aberrations in the plasma DNA for the detection of a specific cancer. Different cancers have a set of typical chromosomal aberrations. Changes (amplifications and deletions) in multiple chromosomal regions may be used. Thus, there would be an increased proportion of sequences aligned to the amplified regions and a decreased proportion of sequences aligned to decreased regions. The percentage representation per chromosome could be compared with the size for each corresponding chromosome in a reference genome expressed as percentage of genomic representation of any given chromosome in relation to the whole genome. Direct comparisons or comparisons to a reference chromosome may also be used.

II. Sequencing Just a Fraction of the Human Genome

In the experiment described in example I above, maternal plasma DNA from each individual specimen was sequenced using one flow cell only. The number of sequenced tags generated from each of the tested specimens by the sequencing run is shown in FIG. 6. T21 denote a sample obtained from a pregnancy involving a trisomy 21 fetus.

As 36 bp were sequenced from each of the sequenced maternal plasma DNA fragments, the number of nucleotides/basepairs sequenced from each specimen could be determined by 36 bp multiplied by the sequenced tag count and are also shown in FIG. 6. As there are approximately 3 billion basepairs in the human genome, the amount of sequencing data generated from each maternal plasma specimen represented only a fraction, ranging from some 10% to 13%.

Furthermore, in this study, only the uniquely mappable sequenced tags, termed U0 in nomenclature from the Eland software, were used to demonstrate the presence of over-representation in the amount of chromosome 21 sequences in the maternal plasma specimens from pregnancies each carrying a fetus with trisomy 21, as described in example I above. As shown in FIG. 6, U0 sequences only represent a subset of all the sequenced tags generated from each specimen and further represent an even smaller proportion, some 2%, of the human genome. These data indicate that the sequencing of only a portion of the human genomic sequences present in the tested specimen is sufficient to achieve the diagnosis of fetal aneuploidy.

III. Determination of Number of Sequences Required

The sequencing result of the plasma DNA from a pregnant woman carrying a euploid male fetus is used for this analysis.

The number of sequenced tags that can be mapped without mismatches to the reference human genome sequence was 1,990,000. Subsets of sequences were randomly chosen from these 1,990,000 tags and the percentage of sequences aligned to chromosome 21 was calculated within each subset. The number of sequences in the subsets was varied from 60,000 to 540,000 sequences. For each subset size, multiple subsets of the same number of sequenced tags were compiled by random selection of the sequenced tags from the total pool until no other combination was possible. The mean percentage of sequences aligned to chromosome 21 and its standard deviation (SD) were then calculated from the multiple subsets within each subset size. These data were compared across different subset sizes to determine the effect of subset size on the distribution of the percentage of sequences aligned to the chromosome 21. The $5^{th}$ and $95^{th}$ percentiles of the percentages were then calculated according to the mean and SD.

When a pregnant woman is carrying a trisomy 21 fetus, the sequenced tags aligned to chromosome 21 should be over-represented in the maternal plasma due to an extra dose of chromosome 21 from the fetus. The degree of over-representation is dependent on the fetal DNA percentage in the maternal plasma DNA sample following the equation below:

$$Per_{T21} = Per_{Eu} \times (1 + f/2)$$

where
$Per_{T21}$ represents the percentage of sequences aligned to chromosome 21 in a woman with a trisomy 21 fetus; and
$Per_{Eu}$ represents the percentage of sequences aligned to chromosome 21 in a woman with a euploid ferns; and
f represents the fetal DNA percentage in maternal plasma DNA As shown in FIG. 7, the SD for the percentages of sequences aligned to chromosome 21 decreases with increasing number of sequences in each subset. Therefore, when the number of sequences in each subset increases, the interval between the $5^{th}$ and $95^{th}$ percentiles decreases. When the 5%-95% interval for the euploid and trisomy 21 cases do not overlap, then the differentiation between the two groups of cases would be possible with an accuracy of >95%.

As shown in FIG. 7, the minimal subset size for the differentiation of trisomy 21 cases from euploid cases is dependent on the fetal DNA percentage. The minimal subset sizes for differentiating trisomy 21 from euploid cases were 120,000, 180,000 and 540,000 sequences for fetal DNA percentages of 20%, 10% and 5%, respectively. In other words, the number of sequences needed to be analyzed would be 120,000 for determining whether a fetus has trisomy 21 when a maternal plasma DNA sample contains 20% fetal DNA. The number of sequences needed to be analyzed would be increased to 540,000 when the fetal DNA percentage drops to 5%.

As the data were generated using 36 basepair sequencing, 120,000, 180,000 and 540,000 sequences correspond to 0.14%, 0.22% and 0.65% of the human genome, respectively. As the lower range of fetal DNA concentrations in maternal plasma obtained from early pregnancies were reported to be some 5% (Lo, Y M D et al. 1998 *Am J Hum Genet* 62, 768-775), the sequencing of about 0.6% of the human genome may represent the minimal amount of sequencing required for diagnosis with at least 95% accuracy in detecting fetal chromosomal aneuploidy for any pregnancy.

IV. Random Sequencing

To illustrate that the sequenced DNA fragments were randomly selected during the sequencing run, we obtained the sequenced tags generated from the eight maternal plasma samples analyzed in example I. For each maternal plasma specimen, we determined the starting positions in relation to the reference human genome sequence, NCBI assembly 36, of each of the 36 bp sequenced tags that were aligned uniquely to chromosome 21 without mismatches. We then ordered the starting position number for the pools of aligned sequenced tags from each specimen in ascending order. We performed a similar analysis for chromosome 22. For illustrative purpose, the top ten starting positions for chromosome 21 and chromosome 22 for each of the maternal plasma specimens are shown in FIGS. 8A and 8B, respectively. As can be appreciated from these Tables, the sequenced pools of DNA fragments were non-identical between samples.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via internet download). Any such computer readable medium may reside on or within a single computer program product (e.g. a hard drive or an entire computer system), and may be present on or within different computer program products within a system or network. A computer system may include a monitor, printer, or other suitable display for providing any of the results mentioned herein to a user.

Figure 9:
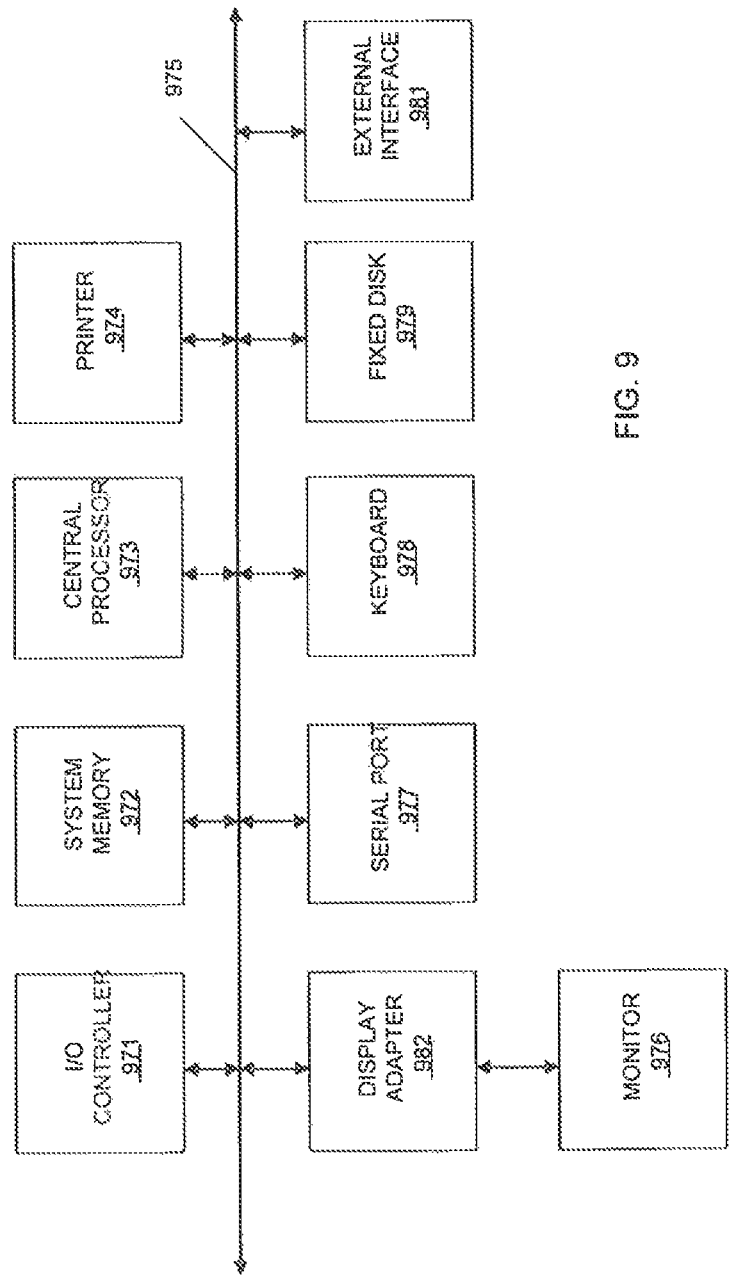
FIG. 9 shows a block diagram of an exemplary computer apparatus usable with system and methods according to embodiments of the present invention.

An example of a computer system is shown in FIG. 9. The subsystems shown in FIG. 9 are interconnected via a system bus 975. Additional subsystems such as a printer 974, keyboard 978, fixed disk 979, monitor 976, which is coupled to display adapter 982, and others are shown. Peripherals and input/output (I/O) devices, which couple to I/O controller 971, can be connected to the computer system by any number of means known in the art, such as serial port 977. For example, serial port 977 or external interface 981 can be used to connect the computer apparatus to a wide area network such as the Internet, a mouse input device, or a scanner. The interconnection via system bus allows the central processor 973 to communicate with each subsystem and to control the execution of instructions from system memory 972 or the fixed disk 979, as well as the exchange of information between subsystems. The system memory 972 and/or the fixed disk 979 may embody a computer readable medium.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

All publications, patents, and patent applications cited herein are hereby incorporated by reference in their entirety for all purposes.

What is claimed is:

1. A method for determining the presence or absence of fetal aneuploidy from a plasma or serum sample from a pregnant female subject, wherein the sample comprises cell-free nucleic acid molecules from the genome of both the female subject and a fetus, comprising:
   (a) performing random massively parallel DNA sequencing on at least a portion of the cell-free nucleic acid molecules to generate random sequenced tags;
   (b) aligning at least a portion of the sequenced tags obtained in step (a) to a reference genome;
   (c) calculating a fractional representation of a first chromosome from sequenced tags aligned to the first chromosome and sequenced tags aligning to one or more second chromosomes;
   (d) comparing the fractional representation of the first chromosome to a cutoff value representing the expected fractional representation in the absence of aneuploidy; and
   (e) based on the comparison step of (d), determining whether fetal aneuploidy is present or absent.

2. The method of claim 1, wherein the random massively parallel DNA sequencing is performed at less than 100% genomic coverage.

3. The method of claim 1, wherein the first chromosome is selected from the group consisting of chromosome 21, chromosome 18, chromosome 13, chromosome X, and chromosome Y.

4. The method of claim 1, wherein the one or more second chromosomes consist of a single chromosome.

5. The method of claim 1, wherein the one or more second chromosomes comprise two or more chromosomes.

6. The method of claim 1, wherein the sequenced cell-free nucleic acid molecules represent a portion of the human genome selected from the group consisting of at least about 0.1%, 0.5%, 1%, 5%, 10%, 20%, and 30% of the human genome.

* * * * *